United States Patent [19]

Sworin et al.

[11] Patent Number: 5,750,088
[45] Date of Patent: May 12, 1998

[54] STABLE HYDRAZONES LINKED TO A PEPTIDE MOIETY AS REAGENTS FOR THE PREPARATION OF RADIOPHARMACEUTICALS

[75] Inventors: Michael Sworin, Tyngsboro; Milind Rajopadhye, Westford, both of Mass.; Thomas David Harris, Salem, N.H.; David Scott Edwards, Burlington, Mass.; Edward Hollister Cheesman, Lunenburg, Mass.; Shuang Liu, Chelmsford, Mass.

[73] Assignee: The DuPont Merck Pharmaceutical Company, Wilmington, Del.

[21] Appl. No.: 476,296

[22] Filed: Jun. 7, 1995

Related U.S. Application Data

[63] Continuation-in-part of Ser. No. 218,861, Mar. 28, 1994, which is a continuation-in-part of Ser. No. 40,336, Mar. 30, 1993, abandoned.

[51] Int. Cl.[6] .............. A61K 51/08; A61K 38/00; C07D 401/00
[52] U.S. Cl. .............. 424/1.69; 424/1.41; 530/300; 530/317; 530/323; 530/332; 544/238; 546/281
[58] Field of Search .............. 424/1.41, 1.45, 424/1.49, 1.53, 1.69, 1.65; 534/10, 15, 16; 530/300, 317, 388.25, 323, 332, 350, 351, 380, 381, 382, 387.1, 388.22, 391.5; 546/281; 544/238; 548/190, 545, 548; 514/565, 632, 639

[56] References Cited

U.S. PATENT DOCUMENTS

| | | |
|---|---|---|
| 4,917,879 | 4/1990 | Deutsch . |
| 4,957,728 | 9/1990 | Deutsch et al. . |
| 5,045,302 | 9/1991 | Kelly et al. . |
| 5,066,789 | 11/1991 | Srinivasan et al. .............. 530/388 |
| 5,112,594 | 5/1992 | Woulfe et al. . |
| 5,206,370 | 4/1993 | Schwartz et al. .............. 546/281 |
| 5,362,852 | 11/1994 | Geoghegan .............. 530/345 |
| 5,549,883 | 8/1996 | Srinivasan et al. .............. 424/1.45 |

FOREIGN PATENT DOCUMENTS

| | | |
|---|---|---|
| 0201005A2 | 4/1986 | European Pat. Off. . |
| 0266910A2 | 10/1987 | European Pat. Off. . |
| 0386873A1 | 1/1990 | European Pat. Off. . |
| 2698272 | 11/1992 | France . |
| 8908657 | 3/1989 | WIPO . |
| 8912640 | 5/1989 | WIPO . |
| 9103262 | 3/1991 | WIPO . |
| 9200982 | 3/1991 | WIPO . |
| 9301839 | 7/1992 | WIPO . |

OTHER PUBLICATIONS

Pasqualini, et al., J. Chem. Soc. Dalton Trans., 3729–3733 (1990).
Pasqualini, et al., Appl. Radiat. Isot., 43, No. 2, 425–436 (1992).
Brinkley, M., Bioconjugate Chemistry, vol. 2, No. 1, 2–13 (1992).
King, et al., Biochemistry, vol. 25, 5774–5779, (1986).
Rando, et al., Journal of Biological Chemistry, vol. 254, 8318–8323 (1979).

*Primary Examiner*—Gary E. Hollinden
*Assistant Examiner*—Michael G. Hartley
*Attorney, Agent, or Firm*—Gerald J. Boudreaux; David H. Vance

[57] ABSTRACT

This invention provides novel reagents for the preparation of radiopharmaceuticals useful as imaging agents for the diagnosis of cardiovascular disorders, infection, inflammation and cancer, diagnostic kits comprising said reagents and intermediate compounds useful for the preparation of said reagents. The reagents are comprised of stable hydrazone modified biologically active molecules that react with gamma emitting radioisotopes to form radiopharmaceuticals that selectively localize at sites of disease and thus allow an image to be obtained of the loci using gamma scintigraphy.

7 Claims, 1 Drawing Sheet

5,750,088

1

STABLE HYDRAZONES LINKED TO A PEPTIDE MOIETY AS REAGENTS FOR THE PREPARATION OF RADIOPHARMACEUTICALS

CROSS-REFERENCE TO RELATED APPLICATIONS

The present application is a continuation-in-part of our application U.S. Ser. No. 08/218,861 filed Mar. 28, 1994, pending which is a continuation-in-part of U.S. Ser. No. 08/040,336 filed Mar. 30, 1993, now abandoned, the disclosures of which are incorporated herein by reference.

FIELD OF THE INVENTION

This invention relates to novel reagents for the preparation of radiopharmaceuticals useful as imaging agents for the diagnosis of cardiovascular disorders, infection, inflammation and cancer, to diagnostic kits comprising said reagents and to intermediate compounds useful for the preparation of said reagents. The reagents are comprised of stable hydrazone modified biologically active molecules that react with gamma emitting radioisotopes to form radiopharmaceuticals that selectively localize at sites of disease and thus allow an image to be obtained of the loci using gamma scintigraphy.

BACKGROUND OF THE INVENTION

There is a current need for new methods for the non-invasive diagnosis of a variety of diseases such as thromboembolic disease, atherosclerosis, infection and cancer. Radiopharmaceuticals comprised of gamma-ray emitting radionuclide labeled biologically active molecules can fulfill the need. The biologically active molecules serve to localize the radionuclides at the sites of disease and thus allow the sites to be visualized by gamma scintigraphy. The molecules can be either proteins, antibodies, antibody fragments, peptides or polypeptides, or peptidomimetics. The molecules interact with a receptor or binding site expressed at the sites of the disease or with a receptor or binding site on an endogenous blood component, such as platelets and leukocytes, that accumulate at the sites. This interaction results in selective localization of a percentage of the injected radiopharmaceutical while the remainder is cleared either through the renal or hepatobiliary systems. The localized radiopharmaceutical is then imaged externally using gamma scintigraphy. The relative rates of localization, clearance and radionuclidic decay determine the ease of visualization, often expressed as the target-to-background ratio. Frequently, only certain portions of the biologically active molecules bind to the receptors; these portions are termed the recognition sequences or units.

A number of radiopharmaceuticals comprised of radionuclide labeled proteins, antibodies or antibody fragments are under development, however, to date only one has been approved by the Food and Drug Administration. This sparse record results from a combination of factors that make developing these radiopharmaceuticals difficult, including problems with manufacturing and quality control, non-optimal sequestration and clearance rates, and the occurence of antigenic or allergic responses to the radiopharmaceuticals. These problems are mainly due to the macromolecular nature of the proteins, antibodies and antibody fragments. Their high molecular weight makes direct chemical synthesis impractical, therefore they must be synthesized by recombinant or cloning techniques that typically give low yields and require extensive isolation and purification procedures. Their molecular weight can slow their rates of localization and preclude their clearance by an active elimination mechanism via the kidneys or liver, resulting in prolonged retention in the circulation which causes a high background level during imaging. Also, the body's immune system tends to recognize more efficiently larger exogenous species.

The use of lower molecular weight peptides, polypeptides or peptidomimetics as the biologically active molecules obviates a number of these problems. These molecules can be synthesized directly using classical solution chemistry or by an automated peptide synthesizer. They can be formed in higher yields and require less complicated purification procedures. They tend to clear more rapidly from the circulation by an active elimination pathway resulting in a lower background in the images. They are also usually not immunogenic. The first radionuclide labeled polypeptide radiopharmaceutical has been recently approved by the Food and Drug Administration.

There are two general methods for labeling biologically active molecules with radionuclides for use as radiopharmaceuticals termed direct and indirect labeling. Direct labeling involves attaching the radionuclide to atoms on the biologically active molecule; while the indirect method involves attaching the radionuclide via a chelator. The chelator can either be attached to the biologically active molecule prior to reaction with the radionuclide or the radionuclide labeled chelator moiety can be attached to the biologically active molecule. Several recent reviews describe these labeling methods and are incorporated herein by reference: S. Jurisson et. al., Chem. Rev., 1993, 93, 1137; A. Verbruggen, Eur. J. Nuc. Med., 1990, 17, 346; and M. Derwanjee, Semin. Nuc. Med., 1990, 20, 5.

The use of hydrazines and hydrazides as chelators to modify proteins for labeling with radionuclides has been recently disclosed in Schwartz et. al., U.S. Pat. No. 5,206, 370. The protein is modified by reaction with bifunctional aromatic hydrazines or hydrazides having a protein reactive substituent. For labeling with technetium-99m, the hydrazino-modified protein is reacted with a reduced technetium species, formed by reacting pertechnetate with a reducing agent in the presence of a chelating dioxygen ligand. The technetium becomes bound to the protein through what are believed to be hydrazido or diazenido linkages with the coordination sphere completed by the ancillary dioxygen ligands. Examples of ancillary dioxygen ligands include glucoheptonate, gluconate, 2-hydroxyisobutyrate, and lactate.

In one embodiment of the invention described in Schwartz et. al., the bifunctional aromatic hydrazine or hydrazide is protected as a lower alkyl hydrazone. This was done to prevent cross-reaction between the hydrazine or hydrazide and the protein reactive substituent because in the absence of the protecting group the bifunctional compound reacts with a protein to form a hydrazone modified protein. The free hydrazine or hydrazide group on the protein is then formed by dialysis into an acidic (pH 5.6) buffer and mixed with a suitable metal species, such as a reduced technetium species, in acidic media to yield a labeled protein.

Although the lower alkyl hydrazone protecting group prevents the cross-reaction between the hydrazine or hydrazide and the protein reactive substituent, it can be displaced by other aldehydes and ketones to form different hydrazones. This is a serious and significant disadvantage. The presence of other aldehydes and ketones in small quantities is unavoidable in a commercial pharmaceutical manufacturing setting. because they are extracted from various plastic and rubber materials and are also used in common disinfectants. Small quantities of formaldehyde are particularly ubiquitous. Therefore, reagents comprised of lower alkyl hydrazone protected biologically active molecules can degrade into a number of different hydrazone containing species, depending on the number and quantities of other aldehydes and ketones to which they are exposed during processing or manufacturing or storage after manufacture. This presents a significant problem in maintaining the purity of the reagents, and thus renders lower alkyl protected reagents unattractive as commercial candidates.

The present invention provides novel reagents for the preparation of radiopharmaceuticals comprised of stable hydrazone modified biologically active molecules. The stable hydrazones do not react appreciably with other aldehydes and ketones, maintaining the purity of the reagents during manufacturing. Surprisingly, these stable hydrazone reagents are still reactive enough to be labeled with radionuclides such as technetium-99m.

SUMMARY OF THE INVENTION

This invention relates to novel reagents for the preparation of radiopharmaceuticals useful as imaging agents for the diagnosis of cardiovascular disorders, infection, inflammation and cancer. The reagents are comprised of stable hydrazone modified biologically active molecules that react with gamma emitting radioisotopes to form radiopharmaceuticals that selectively localize at sites of disease and thus allow an image to be obtained of the loci using gamma scintigraphy. The stable hydrazone serves as a protecting group for the chelator or bonding unit of the reagents preventing decomposition or degradation during the manufacturing process. This invention also provides diagnostic kits comprising such reagents. This invention also provides novel intermediate compounds useful for the preparation of said reagents.

DETAILED DESCRIPTION OF THE INVENTION

Figure 1:
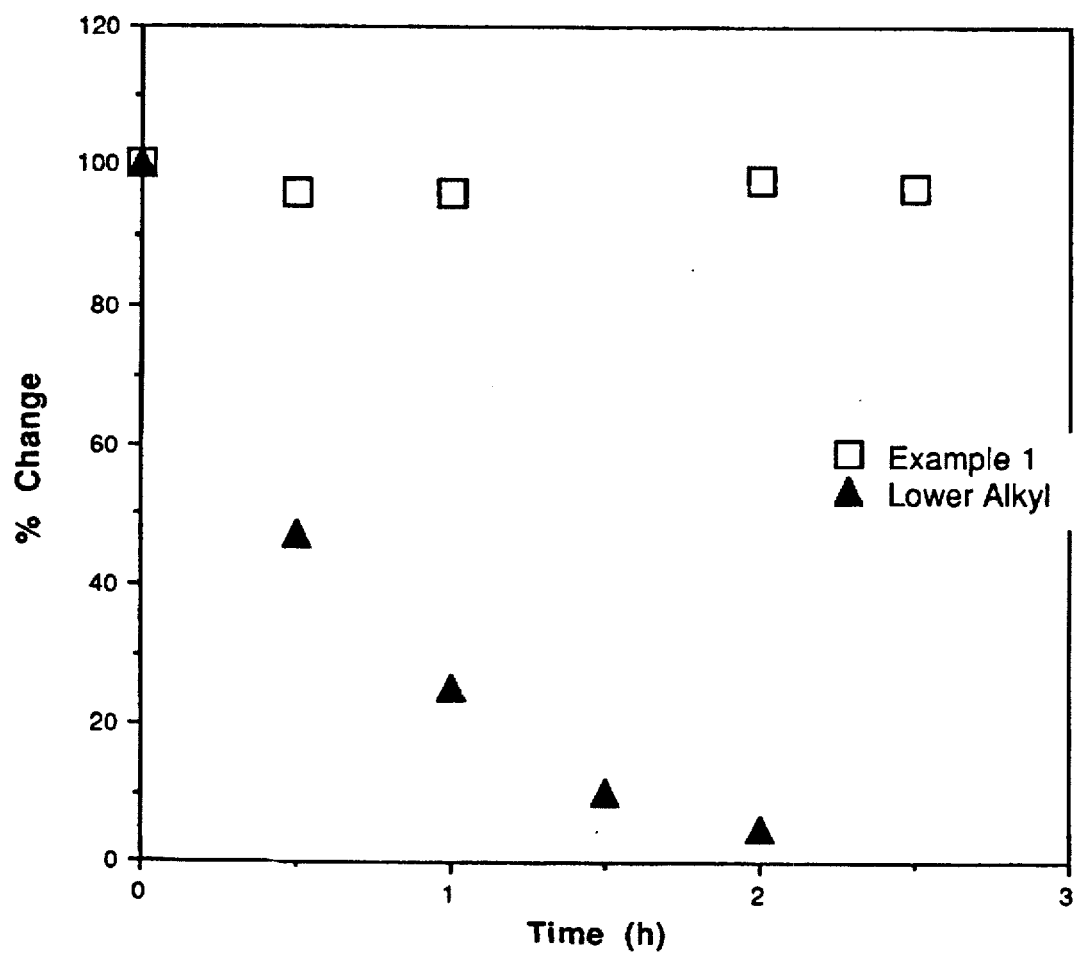
FIGURE 1. A comparison of the stability of the reagent described in Example 1 to 10 equivalents of formaldehyde with that of the lower alkyl hydrazone compound, cyclo-(D-Val-NMeArg-Gly-Asp-Mamb(hydrazino-nicotinyl-5-Aca)) propionaldehyde hydrazone.

This invention provides novel reagents for the preparation of radiopharmaceuticals useful as imaging agents for the diagnosis of cardiovascular disorders, infection, inflammation and cancer, diagnostic kits comprising said reagents and intermediate compounds useful for the preparation of said reagents. The reagents are comprised of stable hydrazone modified biologically active molecules that react with gamma emitting radioisotopes to form radiopharmaceuticals that selectively localize at sites of disease and thus allow an image to be obtained of the loci using gamma scintigraphy.

[1] One embodiment of this invention is a reagent for preparing a radiopharmaceutical comprising a biologically active group connected to a stable hydrazone group, optionally having a linking group between said stable hydrazone and said biologically active group.

[2] Another embodiment of this invention is the reagent of embodiment [1] having a linking group between said stable hydrazone and said biologically active group.

[3] Another embodiment of this invention is the reagent of embodiment [2] having the formula:

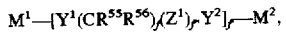

and pharmaceutically acceptable salts thereof wherein,

Q is a biologically active group;
d' is 1–20;
$L_n$ is a linking group of formula:

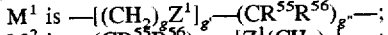

wherein:

$M^1$ is 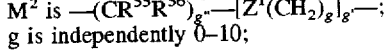
$M^2$ is —$(CR^{55}R^{56})_{g''}$—$[Z^1(CH_2)_g]_{f'}$—;
g is independently 0–10;
g' is independently 0–1;
g" is independently 0–10;
f is independently 0–10;
f' is independently 0–10;
f" is independently 0–1;
$Y^1$ and $Y^2$, are independently selected at each occurrence from: a bond, O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, $(NH)_2C=S$;
$Z^1$ is independently selected at each occurrence from a $C_6$–$C_{14}$ saturated, partially saturated, or aromatic carbocyclic ring system, substituted with 0–4 $R^{57}$; and a heterocyclic ring system, substituted with 0–4 $R^{57}$;
$R^{55}$ and $R^{56}$ are independently selected at each occurrence from: hydrogen; $C_1$–$C_{10}$ alkyl substituted with 0–5 $R^{57}$; alkaryl wherein the aryl is substituted with 0–5 $R^{57}$;
$R^{57}$ is independently selected at each occurrence from the group: hydrogen, OH, $NHR^{58}$, C(=O)$R^{58}$, OC(=O)$R^{58}$, OC(=O)O$R^{58}$, C(=O)O$R^{58}$, C(=O)$NR^{58}$, C=N, $SR^{58}$, $SOR^{58}$, $SO_2R^{58}$, NHC(=O)$R^{58}$, NHC(=O)$NHR^{58}$, NHC(=S)$NHR^{58}$; or, alternatively, when attached to an additional molecule Q, $R^{57}$ is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C(=O)$, $(NH)_2C=S$; and,
$R^{58}$ is independently selected at each occurrence from the group: hydrogen; $C_1$–$C_6$ alkyl; benzyl, and phenyl;

Hz is a stable hydrazone of formula:

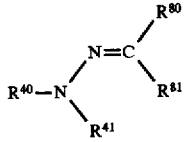

wherein, $R^{40}$ is independently selected at each occurrence from the group: a bond to $L_n$, $C_1$–$C_{10}$ alkyl substituted with 0–3 $R^{52}$, aryl substituted with 0–3 $R^{52}$, cycloaklyl substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52}$;

$R^41$ is independently selected from the group: hydrogen, aryl substituted with 0–3 $R^{52}$, $C_1$–$C_{10}$ alkyl substituted with 0–3 $R^{52}$, and a heterocycle substituted with 0–3 $R^{52}$;

$R^{52}$ is independently selected at each occurrence from the group: a bond to $L_n$, =O, F, Cl, Br, I, —$CF_3$, —CN, —CO$_2$R$^{53}$, —C(=O)R$^{53}$, —C(=O)N(R$^{53}$)$_2$, —CHO, —CH$_2$OR$^{53}$, —OC(=O)R$^{53}$, —OC(=O)OR$^{53a}$, —OR$^{53}$, —OC(=O)N(R$^{53}$)$_2$, —NR$^{53}$C(=O)R$^{53}$, —NR$^{54}$C(=O)OR$^{53a}$, —NR$^{53}$C(=O)N(R$^{53}$)$_2$, —NR$^{54}$SO$_2$N(R$^{53}$)$_2$, —NR$^{54}$SO$_2$R$^{53a}$, —SO$_3$H, —SO$_2$R$^{53a}$, —SR$^{53}$, —S(=O)R$^{53a}$, —SO$_2$N(R$^{53}$)$_2$, —N(R$^{53}$)$_2$, —NHC(=NH)NHR$^{53}$, —C(=NH)NHR$^{53}$, =NOR$^{53}$, NO$_2$, —C(=O)NHOR$^{53}$, —C(=O)NHNR$^{53}$R$^{53a}$, —OCH$_2$CO$_2$H, 2-(1-morpholino)ethoxy;

R$^{53}$, R$^{53a}$, and R$^{54}$ are each independently selected at each occurrence from the group: hydrogen, C$_1$–C$_6$ alkyl, and a bond to L$_n$;

R$^{80}$ and R$^{81}$ are independently selected from the group: H; C$_1$–C$_{10}$ alkyl; —CN; —CO$_2$R$^{85}$; —C(=O)R$^{85}$; —C(=O)N(R$^{85}$)$_2$; C$_2$–C$_{10}$ 1-alkene substituted with 0–3 R$^{84}$; C$_2$–C$_{10}$ 1-alkyne substituted with 0–3 R$^{84}$; aryl substituted with 0–3 R$^{84}$; unsaturated heterocycle substituted with 0–3 R$^{84}$; and unsaturated carbocycle substituted with 0–3 R$^{84}$; provided that when one of R$^{80}$ and R$^{81}$ is H or alkyl, then the other is not H or alkyl;

or, alternatively, R$^{80}$ and R$^{81}$, may be taken together with the shown divalent carbon radical to form:

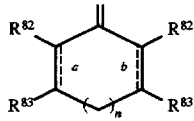

wherein:

R$^{82}$ and R$^{83}$ may be independently selected from the group: H; R$^{84}$; C$_1$–C$_{10}$ alkyl substituted with 0–3 R$^{84}$; C$_2$–C$_{10}$ alkenyl substituted with 0–3 R$^{84}$; C$_2$–C$_{10}$ alkynyl substituted with 0–3 R$^{84}$; aryl substituted with 0–3 R$^{84}$; heterocycle substituted with 0–3 R$^{84}$; and carbocycle substituted with 0–3 R$^{84}$;

or, alternatively, R$^{82}$, R$^{83}$ may be taken together to form a fused aromatic or heterocyclic ring;

a and b indicate the positions of optional double bonds and n is 0 or 1.

R$^{84}$ is independently selected at each occurrence from the group: =O, F, Cl, Br, I, —CF$_3$, —CN, —CO$_2$R$^{85}$, —C(=O)R$^{85}$, —C(=O)N(R$^{85}$)$_2$, —N(R$^{85}$)$_3^+$, —CH$_2$OR$^{85}$, —OC(=O)R$^{85}$, —OC(=O)OR$^{85a}$, —OR$^{85}$, —OC(=O)N(R$^{85}$)$_2$, —NR$^{85}$C(=O)R$^{85}$, —NR$^{86}$C(=O)OR$^{85a}$, —NR$^{85}$C(=O)N(R$^{85}$)$_2$, —NR$^{86}$SO$_2$N(R$^{85}$)$_2$, —NR$^{86}$SO$_2$R$^{85a}$, —SO$_3$H, —SO$_2$R$^{85a}$, —SR$^{85}$, —S(=O)R$^{85a}$, —SO$_2$N(R$^{85}$)$_2$, —N(R$^{85}$)$_2$, —NHC(=NH)NHR$^{85}$, —C(=NH)NHR$^{85}$, =NOR$^{85}$, —C(=O)NHOR$^{85}$, —OCH$_2$CO$_2$H, 2-(1-morpholino)ethoxy; and R$^{85}$, R$^{85a}$, and R$^{86}$ are each independently selected at each occurrence from the group: hydrogen, C$_1$–C$_6$ alkyl.

[4] Another embodiment of this invention is the reagent of embodiment [3] wherein:

Q is a biologically active molecule selected from the group: IIb/IIIa receptor antagonists, IIb/IIIa receptor ligands, fibrin binding peptides, leukocyte binding peptides, chemotactic peptides, somatostatin analogs, and selectin binding peptides;

d' is 1 to 3;

L$_n$ is:

—(CR$^{55}$R$^{56}$)$_{g''}$—[Y$^1$(CR$^{55}$R$^{56}$)$_{f'}$Y$^2$]$_{f'}$—(CR$^{55}$R$^{56}$)$_{g''}$—.

wherein:

g" is 0–5;

f is 0–5;

f' is 1–5;

Y$^1$ and Y$^2$, are independently selected at each occurrence from: O, NR$^{56}$, C=O, C(=O)O, OC(=O)O, C(=O)NH—, C=NR$^{56}$, S, SO, SO$_2$, SO$_3$, NHC(=O), (NH)$_2$C(=O), (NH)$_2$C=S;

R$^{55}$ and R$^{56}$ are independently selected at each occurrence from: hydrogen, C$_1$–C$_{10}$ alkyl, and alkaryl;

H$_z$ is a stable hydrazone of formula:

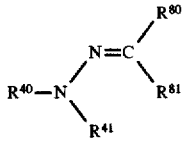

wherein,

R$^{40}$ is independently selected at each occurrence from the group: aryl substituted with 0–3 R$^{52}$, and heterocycle substituted with 0–3 R$^{52}$;

R$^{41}$ is independently selected from the group: hydrogen, aryl substituted with 0–1 R$^{52}$, C$_1$–C$_3$ alkyl substituted with 0–1 R$^{52}$, and a heterocycle substituted with 0–1 R$^{52}$;

R$^{52}$ is independently selected at each occurrence from the group: a bond to L$_n$, —CO$_2$R$^{53}$, —CH$_2$OR$^{53}$, —SO$_3$H, —SO$_2$R$^{53a}$, —N(R$^{53}$)$_2$, —NHC(=NH)NHR$^{53}$, and —OCH$_2$CO$_2$H;

R$^{53}$, R$^{53a}$ are each independently selected at each occurrence from the group: hydrogen and C$_1$–C$_3$ alkyl;

R$^{80}$ is independently selected at each occurrence from the group:

—CO$_2$R$^{85}$;

C$_2$–C$_5$ 1-alkene substituted with 0–3 R$^{84}$;

C$_2$–C$_5$ 1-alkyne substituted with 0–3 R$^{84}$;

aryl substituted with 0–3 R$^{84}$;

unsaturated heterocycle substituted with 0–3 R$^{84}$;

R$^{81}$ is independently selected at each occurrence from the group: H and C–C$_5$ alkyl;

or, alternatively, R$^{80}$ and R$^{81}$, when taken together with the indicated divalent carbon radical form

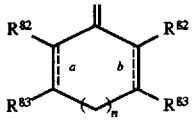

wherein R$^{82}$ and R$^{83}$ may be independently selected from the group: H and R$^{84}$;

or, alternatively, R$^{82}$, R$^{83}$ may be taken together to form a fused aromatic or heterocyclic ring;

a and b indicate the positions of optional double bonds and n is 0 or 1.

R$^{84}$ is independently selected at each occurrence from the group: —CO$_2$R$^{85}$, —C(=O)N(R$^{85}$)$_2$, —CH$_2$OR$^{85}$, —OC(=O)R$^{85}$ —OR$^{85}$, —SO$_3$H, —N(R$^{85}$)$_2$, —OCH$_2$CO$_2$H;

R$^{85}$ is independently selected at each occurrence from the group: hydrogen, C$_1$–C$_3$ alkyl.

[5] Another embodiment of this invention is the reagent of embodiment [4] wherein:

Q represents a biologically active molecule selected from the group: IIb/IIIa receptor antagonists and chemotactic peptides;

d' is 1;

$L_n$ is:
—$(CR^{55}R^{56})_{g''}$—$[Y^1(CR^{55}R^{56})_fY^2]_{f'}$—$(CR^{55}R^{56})_{g''}$—, wherein:

g" is 0–5;
f is 0–5;
f' is 1–5;
$Y^1$ and $Y^2$, at each occurrence, are independently selected from:
O, $NR^{56}$, C=O, C(=O)O, OC(=O)O, C(=O)NH—, C=$NR^{56}$, S, NHC(=O), $(NH)_2C$(=O), (NH)$_2$C=S;
$R^{55}$ and $R^{56}$ are hydrogen;
$H_z$ is a stable hydrazone of formula:

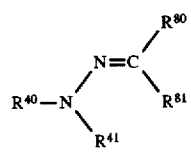

wherein, $R^{40}$ is independently selected at each occurrence from the group: heterocycle substituted with $R^{52}$;

$R^{41}$ is hydrogen;

$R^{52}$ is a bond to $L_n$;

$R^{80}$ is independently selected from the group:
—$CO_2R^{85}$;
$C_2$–$C_3$ 1-alkene substituted with 0–1 $R^{84}$;
aryl substituted with 0–1 $R^{84}$;
unsaturated heterocycle substituted with 0–1 $R^{84}$;

$R^{81}$ is H;

$R^{84}$ is independently selected at each occurrence from the group:
—$CO_2R^{85}$;
—$OR^{85}$;
—$SO_3H$;
—$N(R^{85})_2$;

$R^{85}$ is independently selected at each occurrence from the group:
H and methyl.

[6] Another embodiment of this invention are the reagents of embodiment [3] that are:

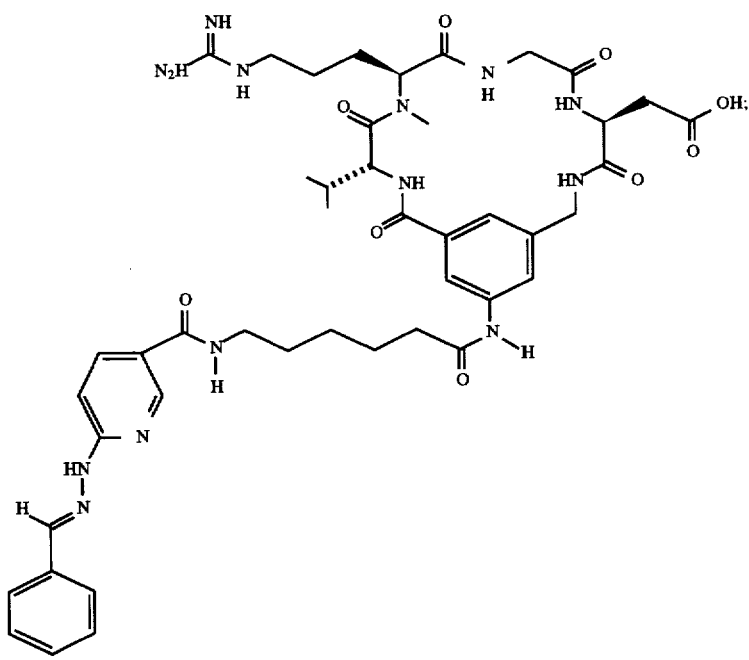

-continued
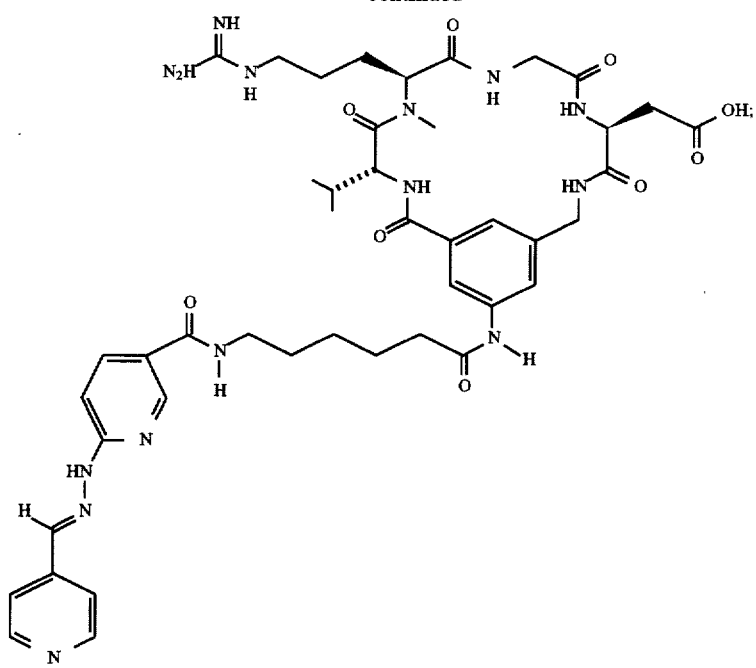
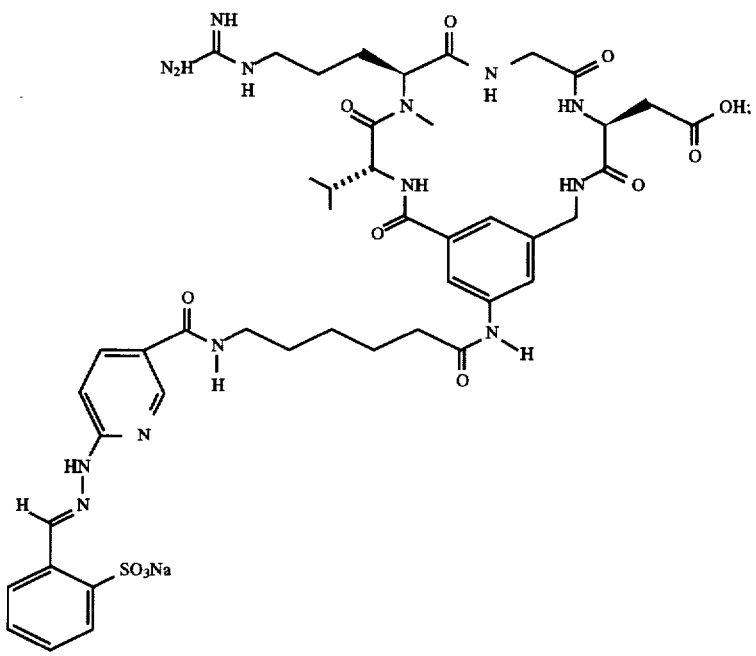

-continued
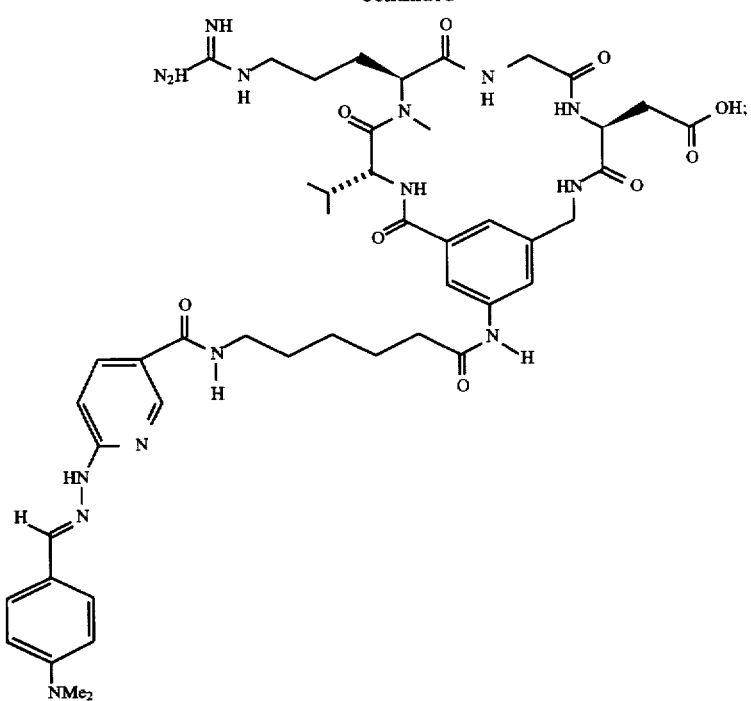
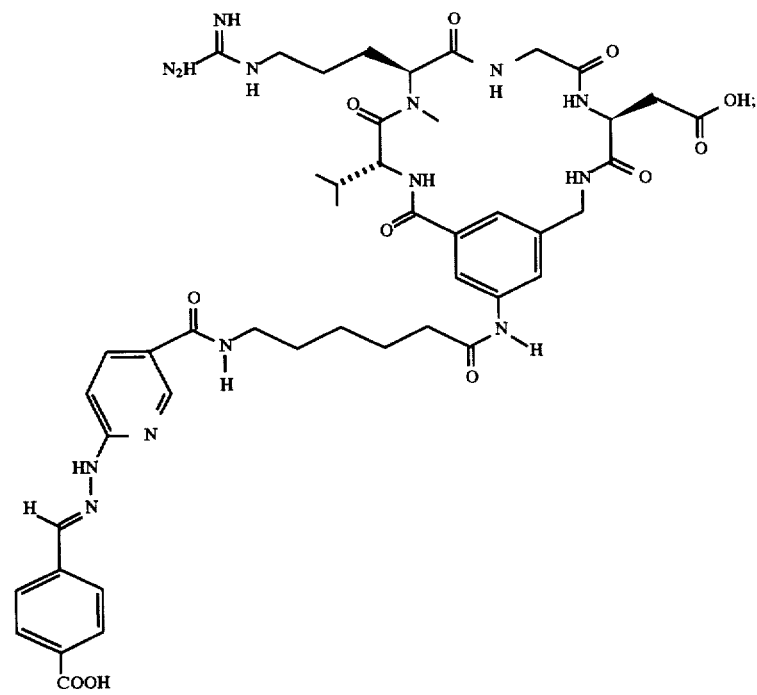

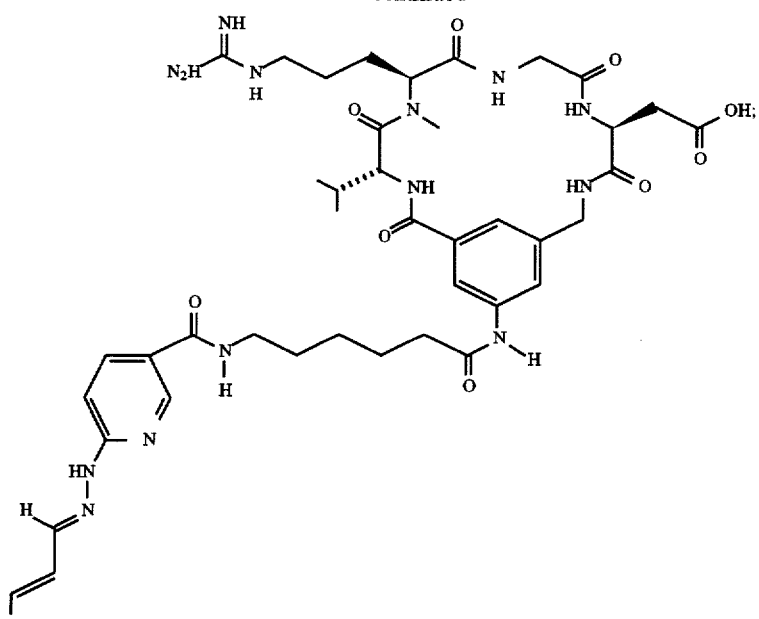
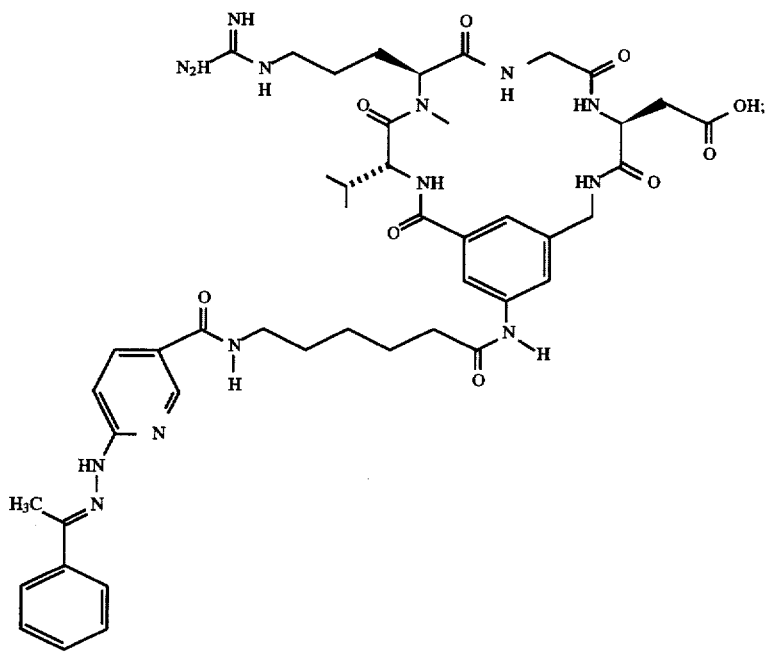

-continued
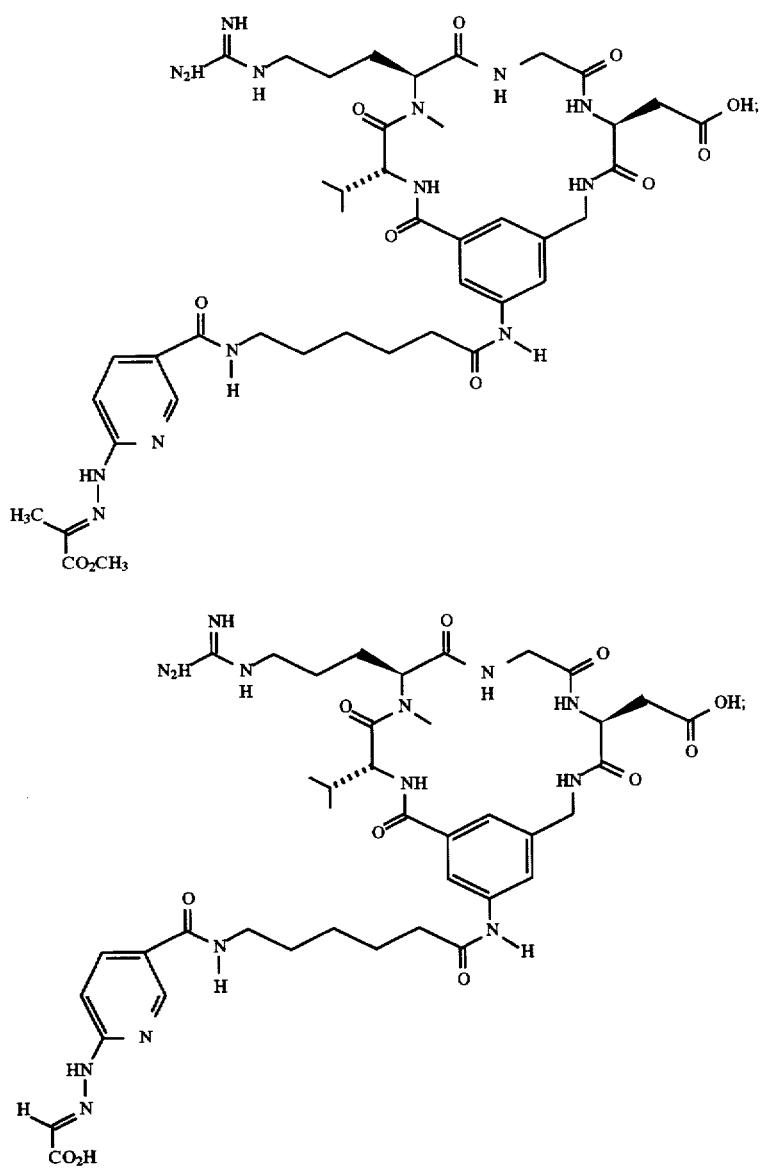

-continued

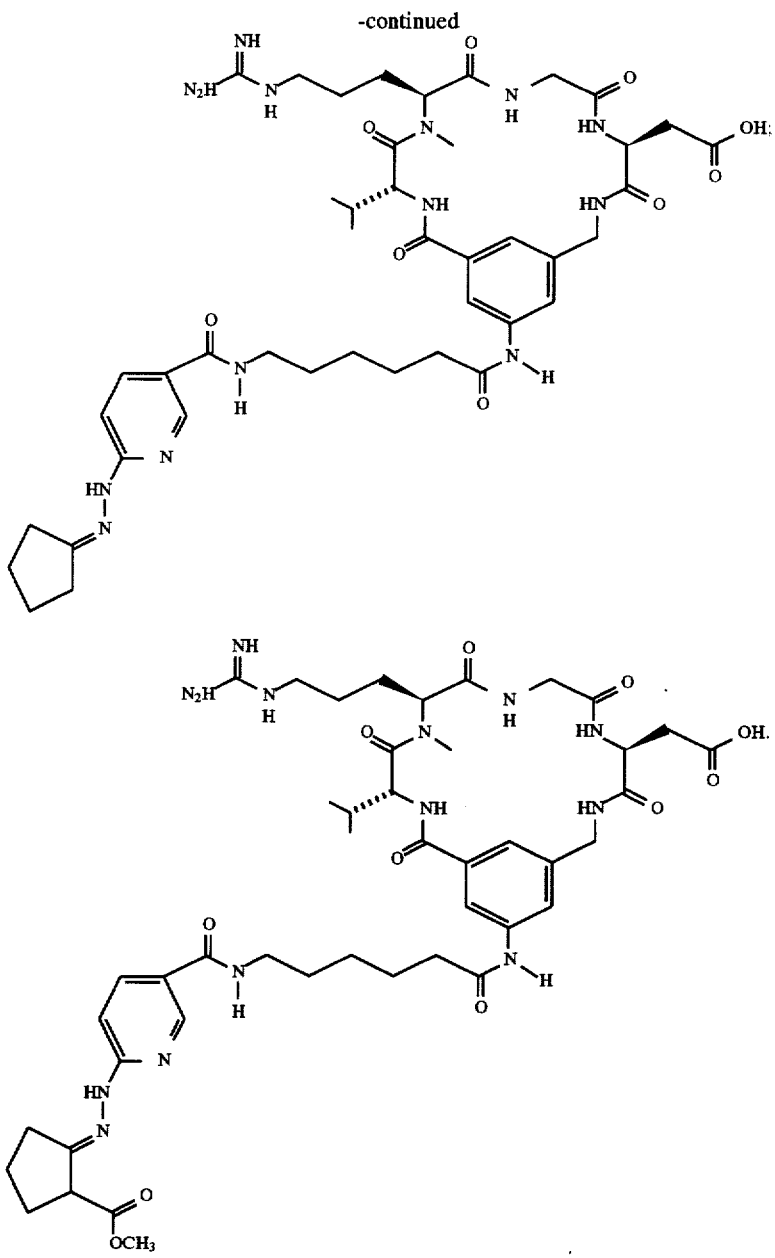

[7] Another embodiment of this invention is a kit for preparing a radiopharmaceutical comprising:
 (a) a predetermined quantity of a sterile, pharmaceutically acceptable reagent of any of claims 1–6;
 (b) a predetermined quantity of one or more sterile, pharmaceutically acceptable ancillary ligand(s);
 (c) a predetermined quantity of a sterile, pharmaceutically acceptable reducing agent; and
 (d) optionally, a predetermined quantity of a sterile, pharmaceutically acceptable component selected from the group: transfer ligands, buffers, lyophilization aids, stabilization aids, solubilization aids and bacteriostats.

[8] Another embodiment of this invention is a kit for preparing a radiopharmaceutical comprising:
 (a) a predetermined quantity of a sterile, pharmaceutically acceptable reagent of any of claims 1–6;
 (b) a predetermined quantity of two sterile, pharmaceutically acceptable ancillary ligand(s);
 (c) a predetermined quantity of a sterile, pharmaceutically acceptable reducing agent; and
 (d) optionally, a predetermined quantity of a sterile, pharmaceutically acceptable component selected from the group:
 transfer ligands, buffers, lyophilization aids, stabilization aids, solubilization aids and bacteriostats.

[9] Another embodiment of this invention is a stable hydrazone compound useful for the synthesis of the reagents of embodiment [1–6] having the formula:

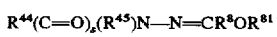

wherein:
 s is 0 or 1;
 $R^{44}$ is selected from the group: aryl substituted with 1 $R^{59}$; and heterocycle substituted with 1 $R^{59}$;
 $R^{45}$ is selected from the group: hydrogen and $C_1$–$C_6$ alkyl,

19

$R^{59}$ is a chemically reactive moiety selected from the group:
  alkyl substituted with halogen;
  acid anhydride;
  acid halide;
  active ester;
  isothiocyanate;
  maleimide;

$R^{80}$ and $R^{81}$ are independently selected from the group:
  H;
  $C_1$–$C_{10}$ alkyl;
  —CN;
  —$CO_2R^{85}$;
  —C(=O)$R^{85}$;
  —C(=O)N($R^{85}$)$_2$;
  $C_2$–$C_{10}$ 1-alkene substituted with 0–3 $R^{84}$;
  $C_2$–$C_{10}$ 1-alkyne substituted with 0–3 $R^{84}$;
  aryl substituted with 0–3 $R^{84}$;
  unsaturated heterocycle substituted with 0–3 $R^{84}$; and
  unsaturated carbocycle substituted with 0–3 $R^{84}$;
  provided that when one of $R^{80}$ and $R^{81}$ is H or alkyl, then the other is not H or alkyl;
or, alternatively, $R^{80}$ and $R^{81}$, may be taken together with the shown divalent carbon radical to form:

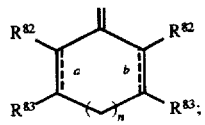

wherein:
  $R^{82}$ and $R^{83}$ are independently selected at each occurrence from the group:
    H;
    $R^{84}$;
    $C_1$–$C_{10}$ alkyl substituted with 0—3 $R^{84}$;
    $C_2$–$C_{10}$ alkenyl substituted with 0–3 $R^{84}$;
    $C_2$–$C_{10}$ alkynyl substituted with 0–3 $R^{84}$;
    aryl substituted with 0–3 $R^{84}$;
    heterocycle substituted with 0–3 $R^{84}$; and
    carbocycle substituted with 0–3 $R^{84}$;
or, alternatively,
  $R^{82}$, $R^{83}$ may be taken together to form a fused aromatic or heterocyclic ring; and
  a and b indicate the positions of optional double bonds;
  n is 0 or 1.
$R^{84}$ is independently selected at each occurrence from the group: =O, F, Cl, Br, I, —$CF_3$, —CN, —$CO_2R^{85}$, —C(=O)$R^{85}$, —C(=O)N($R^{85}$)$_2$, —$CH_2OR^{85}$, —OC(=O)$R^{85}$, —OC (=O) $OR^{85a}$, —$OR^{85}$, —OC(=O)N($R^{85}$)$_2$, —$NR^{85}$C(=O) $R^{85}$, —$NR^{86}$C(=O)$OR^{85a}$, —$NR^{85}$C(=O)N($R^{85}$)$_2$, —$SO_3$Na, —$NR^{86}SO_2N(R^{85})_2$, —$NR^{86}SO_2R^{85a}$, —$SO_3$H, —$SO_2R^{85a}$, —$SR^{85}$, —S(=O)$R^{85a}$, —$SO_2N(R^{85})_2$, —N($R^{85}$)$_2$, N($R^{85}$)$_3^+$, —NHC(=NH)$NHR^{85}$, —C(=NH)$NHR^{85}$, =$NOR^{85}$, —C(=O)$NHOR^{85}$, —$OCH_2CO_2H$, 2-(1-morpholino)ethoxy;
$R^{85}$, $R^{85a}$, and $R^{86}$ are independently selected at each occurrence from the group: hydrogen, $C_1$–$C_6$ alkyl.

[10] Another embodiment of this invention is the compound of embodiment [9] wherein:
  s=0;

20

$R^{59}$ is selected from the group:

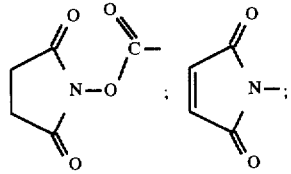

$R^{80}$ is independently selected from the group:
  —$CO_2R^{85}$;
  $C_2$–$C_5$ 1-alkene substituted with 0–3 $R^{84}$;
  $C_2$–$C_5$ 1-alkyne substituted with 0–3 $R^{84}$;
  aryl substituted with 0–3 $R^{84}$;
  unsaturated heterocycle substituted with 0–3 $R^{84}$;
  $R^{81}$ is independently selected from the group: H and $C_1$–$C_5$ alkyl;
or, alternatively, $R^{80}$ and $R^{81}$, may be taken together with the shown divalent carbon radical to form

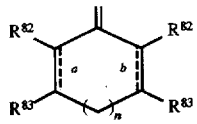

wherein $R^{82}$ and $R^{83}$ may be independently selected from the group: H and $R^{84}$;
or, alternatively, $R^{82}$, $R^{83}$ may be taken together to form a fused aromatic or heterocyclic ring; and
a and b indicate the positions of optional double bonds;
n is 0 or 1.
$R^{84}$ is independently selected at each occurrence from the group: —$CO_2R^{85}$, —C(=O)N($R^{85}$)$_2$, —$CH_2OR^{85}$, —OC(=O)$R^{85}$, —$OR^{85}$, —$SO_3$H, —$SO_3$Na, —N($R^{85}$)$_2$, —$OCH_2CO_2H$;
$R^{85}$ is independently selected at each occurrence from the group: hydrogen and $C_1$–$C_3$ alkyl.

[11] Another embodiment of this invention is the compound of embodiment [10] wherein:
  $R^{80}$ is independently selected from the group:
    —$CO_2R^{85}$;
    $C_2$–$C_3$ 1-alkene substituted with 0–1 $R^{84}$;
    aryl substituted with 0–1 $R^{84}$;
    unsaturated heterocycle substituted with 0–1 $R^{84}$;
  $R^{81}$ is H;
  $R^{84}$ is independently selected at each occurrence from the group: —$CO_2R^{85}$, —$OR^{85}$, —$SO_3$H, —$SO_3$Na, —N($R^{85}$)$_2$;
  $R^{85}$ is independently selected at each occurrence from the group:
    H and methyl.

[12] Another embodiment of this invention are the compounds of embodiment [9] that are:

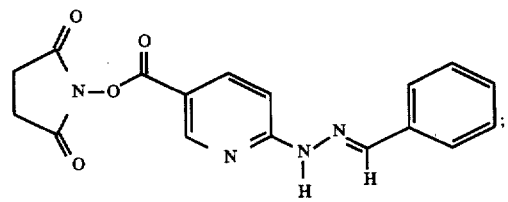

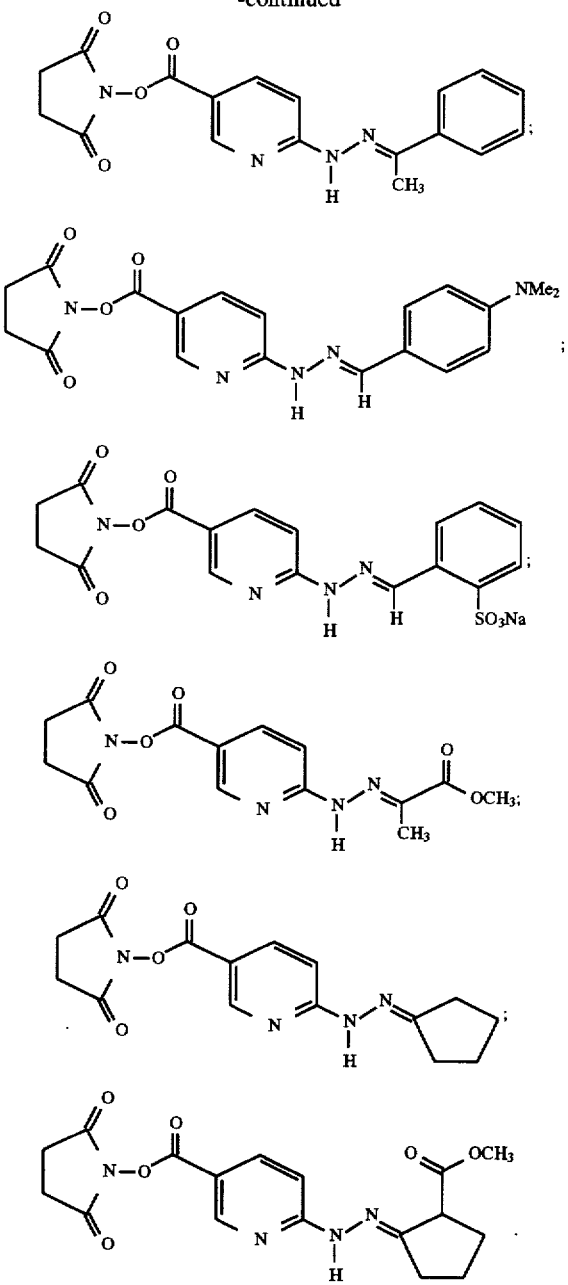

When any variable occurs more than one time in any constituent or in any formula, its definition on each occurrence is independent of its definition at every other occurrence. Thus, for example, if a group is shown to be substituted with 0–2 $R^{52}$, then said group may optionally be substituted with up to two $R^{52}$ and $R^{52}$ at each occurrence is selected independently from the defined list of possible $R^{52}$. Also, by of example, for the group —N($R^{53}$)$_2$, each of the two $R^{53}$ substituents on N is independently selected from the defined list of possible $R^{53}$. Combinations of substituents and/or variables are permissible only if such combinations result in stable compounds.

By "stable compound" or "stable structure" is meant herein a compound that is sufficiently robust to survive isolation to a useful degree of purity from a reaction mixture, and formulation into an efficacious diagnostic agent.

The term "hydrazone", as used herein, means that the moiety, group or compound so described is comprised of at least one divalent carbon radical (or methylene group) bound to a nitrogen atom on a hydrazine or hydrazide through a double bond.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single, double or triple bond.

As used herein, "alkyl" is intended to include both branched and straight-chain saturated aliphatic hydrocarbon groups having the specified number of carbon atoms; "cycloalkyl" or "carbocycle" is intended to include saturated ring groups, including mono-,bi- or poly-cyclic ring systems, such as cyclopropyl, cyclobutyl, cyclopentyl, cyclohexyl, cycloheptyl, cyclooctyl and adamantyl; "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth;

As used herein, the term "alkene" or "alkenyl" is intended to include both branched and straight-chain groups of the formula $C_nH_{2n-1}$ having the specified number of carbon atoms. The term "1-alkene" or "1-alkenyl" means that the double bond is between the first and second carbon atoms from the point of attachment.

As used herein, the term "alkyne" or "alkynyl" is intended to include both branched and straight-chain groups of the formula $C_nH_{2n-3}$ having the specified number of carbon atoms. The term "1-alkyne" or "1-alkynyl" means that the triple bond is between the first and second carbon atoms from the point of attachment.

As used herein, "aryl" or "aromatic residue" is intended to mean phenyl or naphthyl, which when substituted, the substitution can be at any position.

As used herein, the term "heterocycle" or "heterocyclic ring system" is intended to mean a stable 5- to 7- membered monocyclic or bicyclic or 7- to 10-membered bicyclic heterocyclic ring which may be saturated, partially unsaturated, or aromatic, and which consists of carbon atoms and from 1 to 4 heteroatoms selected independently from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofuran, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H,6H-1,5, 2-dithiazine, thiophene, tetrahydrothiophene, thianthrene, furan, pyran, isobenzofuran, chromene, xanthene, phenoxathiin, 2H-pyrrole, pyrrole, imidazole, pyrazole, thiazole, isothiazole, oxazole (including 1,2,4- and 1,3,4- oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine, phenarsazine, phenothiazine, furazan, phenoxazine, isochroman, chroman, pyrrolidine, pyrroline, imidazolidine, imidazoline, pyrazolidine, pyrazoline, piperazine, indoline, isoindoline, quinuclidine, or morpholine. Also included are fused ring and spiro compounds containing, for example, the above heterocycles.

As used herein to describe the substituents $R^{80}$ and $R^{81}$, the term "unsaturated carbocycle" means a carbocycle that has at least one multiple bond, that one multiple bond being between the carbon atom attached to the divalent carbon radical specified in the formula of the stable hydrazone moiety and an adjacent carbon atom.

As used herein to describe the substituents $R^{80}$ and $R^{81}$, the term "unsaturated heterocycle" means a heterocycle that has at least one multiple bond, that one multiple bond being between the carbon atom attached to the divalent carbon radical specified in the formula of the stable hydrazone moiety and an adjacent carbon atom. An aromatic heterocycle is considered an unsaturated heterocycle.

The term "salt", as used herein, is used as defined in the *CRC Handbook of Chemistry and Physics, 65th Edition*, CRC Press, Boca Raton, Fla., 1984, as any substance which yields ions, other than hydrogen or hydroxyl ions.

A "reducing agent" is a compound that reacts with the radionuclide, which is typically obtained as a relatively unreactive, high oxidation state compound, to lower its oxidation state by transfering electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with the radionuclide that is stable enough to prevent unwanted side-reactions but labile enough to be converted to the radiopharmaceutical. The formation of the intermediate complex is kinetically favored while the formation of the radiopharmaceutical is thermodynamically favored. Transfer ligands useful in the preparation of radiopharmaceuticals and in diagnostic kits useful for the preparation of said radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into the radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system. Co-pending application U.S. Ser. No. 08/415,908,908, which is incorporated herein by reference, discloses and teaches ancillary ligands.

A "chelator" or "bonding unit" is the moiety or group on a reagent that binds to a metal radionuclide through the formation of chemical bonds with one or more donor atoms.

The term "binding site" means the site in vivo that binds a biologically active molecule.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "diagnostic kit" comprises a collection of components, termed the formulation, in one or more vials which are used by the practising end user in a clinical or pharmacy setting to synthesize the radiopharmaceutical. The kit provides all the requisite components to synthesize and use the radiopharmaceutical except those that are commonly available to the practising end user, such as water or saline for injection, a solution of the radionuclide, equipment for heating the kit during the synthesis of the radiopharmaceutical if required, equipment necessary for administering the radiopharmaceutical to the patient such as syringes and shielding, and imaging equipment.

A "buffer" is a compound that is used to control the pH of the kit during its manufacture and during the synthesis of the radiopharmaceutical.

A "lyophilization aid" is a component that has favorable physical properties for lyophilization, such as the glass transition temperature, and is added to the diagnostic kit to improve the physical properties of the combination of all the components of the kit for lyophilization.

A "stabilization aid" is a component that is added to the radiopharmaceutical or to the diagnostic kit either to stabilize the radiopharmaceutical once it is synthesized or to prolong the shelf-life of the kit before it must be used. Stabilization aids can be antioxidants, reducing agents or radical scavengers and can provide improved stability by reacting preferentially with species that degrade other components or the radiopharmaceutical.

A "solubilization aid" is a component that improves the solubility of one or more other components in the medium required for the synthesis of the radiopharmaceutical.

A "bacteriostat" is a component that inhibits the growth of bacteria in the diagnostic kit either during its storage before use of after the kit is used to synthesize the radiopharmaceutical.

The following abbreviations are used in this application:

| | |
|---|---|
| Acm | acetamidomethyl |
| D-Abu | D-2-aminobutyric acid |
| 5-Aca | 5-aminocaproamide (5-aminohexanamide) |
| b-Ala, b-Ala or bAla | 3-aminopropionic acid |
| Boc | t-butyloxycarbonyl |
| Boc-iodo-Mamb iodo- | t-butyloxycarbonyl-3-aminomethyl-4-benzoic acid |
| Boc-Mamb | t-butyloxycarbonyl-3-aminomethylbenzoic acid |
| Boc-ON | [2-(tert-butyloxycarbonyloxylimino)-2-phenylacetonitrile |
| Cl$_2$Bzl | dichlorobenzyl |
| CBZ, Cb or Z | Carbobenzyloxy |
| DCC | dicyclohexylcarbodiimide |
| DIEA | diisopropylethylamine |
| di-NMeOrn | N-aMe-N-gMe-ornithine |
| DMAP | 4-dimethylaminopyridine |
| HBTU | 2-(1H-Benzotriazol-1-yl)-1,1,3,3-tetramethyluronium hexafluorophosphate |
| Hynic | hydrazinonicotinyl |
| NMeArg or MeArg | a-N-methyl arginine |
| NMeAmf | N-Methylaminomethylphenylalanine |
| NMeAsp | a-N-methyl aspartic acid |
| NMeGly or MeGly | N-methyl glycine |
| NMe-Mamb | N-methyl-3-aminomethylbenzoic acid |
| NMM | N-methylmorpholine |
| OcHex | O-cyclohexyl |
| OBzl | O-benzyl |
| oSu | O-succinimidyl |
| pNP | p-nitrophenyl |
| TBTU | 2-(1H-Benzotriazol-1-yl)-1,1,3,3-tetramethyluronium tetrafluoroborate |
| Teoc | 2-(Trimethylsilyl)ethyloxycarbonyl |
| Tos | tosyl |
| TPPTS | tris(3-sulfonatophenyl)phosphine trisodium salt |
| Tr | trityl |

The following conventional three-letter amino acid abbreviations are used herein; the conventional one-letter amino acid abbreviations are not used herein:

Ala=alanine
Arg=arginine
Asn=asparagine
Asp=aspartic acid
Cys=cysteine
Gln=glutamine
Glu=glutamic acid
Gly=glycine
His=histidine
Ile=isoleucine
Leu=leucine
Lys=lysine
Met=methionine
Nle=norleucine
Phe=phenylalanine
Phg=phenylglycine
Pro=proline
Ser=serine
Thr=threonine
Trp=tryptophan
Tyr=tyrosine
Val=valine The biologically active molecule Q can be a protein, antibody, antibody fragment, peptide or polypeptide, or peptidomimetic that is comprised of a recognition sequence or unit for a receptor or binding site expressed at the site of the disease, or for a receptor or binding site expressed on platelets or leukocytes. The exact chemical composition of Q is selected based on the disease state to be diagnosed, the mechanism of localization to be utilized, and to provide an optimum combination of rates of localization, clearance and radionuclidic decay.

For the purposes of this invention, the term thromboembolic disease is taken to include both venous and arterial disorders and pulmonary embolism, resulting from the formation of blood clots.

For the diagnosis of thromboembolic disorders or atherosclerosis, Q is selected from the group including the cyclic IIb/IIIa receptor antagonist compounds described in co-pending U.S. Ser. No. 08/415,908,861 (equivalent to WO 94/22494); the RGD containing peptides described in U.S. Pat. Nos. 4,578,079, 4,792,525, the applications PCT US88/04403, PCT US89/01742, PCT US90/03788, PCT US91/02356 and by Ojima et. al., 204th Meeting of the Amer. Chem. Soc., 1992, Abstract 44; the peptides that are fibrinogen receptor antagonists described in European Patent Applications 90202015.5, 90202030.4, 90202032.2, 90202032.0, 90311148.2, 90311151.6, 90311537.6, the specific binding peptides and polypeptides described as IIb/IIIa receptor ligands, ligands for the polymerization site of fibrin, laminin derivatives, ligands for fibrinogen, or thrombin ligands in PCT WO 93/23085 (excluding the technetium binding groups); the oligopeptides that correspond to the IIIa protein described in PCT WO90/00178; the hirudin-based peptides described in PCT WO90/03391; the IIb/IIIa receptor ligands described in PCT WO90/15818; the thrombus, platelet binding or atherosclerotic plaque binding peptides described in PCT WO92/13572 (excluding the technetium binding group) or GB 9313965.7; the fibrin binding peptides described in U.S. Pat. Nos. 4,427,646 and 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in European Patent Application 0478328A1, and by Hartman et. al., J. Med. Chem., 1992, 35, 4640; or oxidized low density lipoprotein (LDL).

For the diagnosis of infection, inflammation or transplant rejection, Q is selected from the group including the leukocyte binding peptides described in PCT WO93/17719 (excluding the technetium binding group), PCT WO92/13572 (excluding the technetium binding group) or U.S. Ser. No. 08-140000; the chemotactic peptides described in Eur. Pat. Appl. 90108734.6 or A. Fischman et. al., Semin. Nuc. Med., 1994, 24, 154; or the leukostimulatory agents described in U.S. Pat. No. 5,277,892.

For the diagnosis of cancer, Q is selected from the group of somatostatin analogs described in UK Application 8927255.3 or PCT WO94/00489, the selectin binding peptides described in PCT WO94/05269, the biological-function domains described in PCT WO93/12819, Platelet Factor 4 or the growth factors (PDGF, EGF, FGF, TNF, MCSF or Il1-8).

Q may also represent proteins, antibodies, antibody fragments, peptides, polypeptides, or peptidomimetics that bind to receptors or binding sites on other tissues, organs, enzymes or fluids. Examples include the β-amyloid proteins that have been demonstrated to accumulate in patients with Alzheimer's disease, atrial naturetic factor derived peptides that bind to myocardial and renal receptors, antimyosin antibodies that bind to areas of infarcted tissues, or nitroimidazole derivatives that localize in hypoxic areas in vivo.

The reagents of the present invention are comprised of a biologically active group, Q, attached to a stable hydrazone, $H_z$, and optionally comprising a linking group, $L_n$, between said biologically active group and said stable hydrazone. The stable hydrazone is a protected form of a hydrazine or hydrazide chelator or bonding unit, designated as $C_h$ in co-pending U.S. Ser. No. 08/415,908,861, that is either directly attached to the moiety Q or is attached to the linking group $L_n$ which is attached to Q. The chelator or bonding unit becomes bound to the radionuclide (and is designated $C_{h'}$ in the bound state in U.S. Ser. No. 08/415,908,908) in the radiopharmaceuticals synthesized using the reagents of the present invention.

The substituents $R^{80}$ and $R^{81}$ of this invention are chosen to improve the stability of the hydrazone over that achievable using substituents comprised solely of hydrogen or lower alkyl. The improved stability is necessary because hydrazones in which the substituents are solely hydrogen or lower alkyl are reactive with other aldehydes and ketones, a number of which are commonly found in a pharmaceutical manufacturing setting. A particularly ubiquitous aldehyde is formaldehyde, which is commonly used in disinfectants. The reaction of a lower alkyl hydrazone with an aldehyde or ketone can proceed as shown in Scheme 1.

Scheme 1

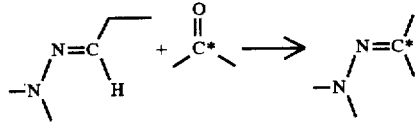

The stable hydrazone protected reagents of this invention may be commercialized as radiopharmaceutical precursors. Lower alkyl protected hydrazones can not be so commercialized, due to their inherent instability. If the lower alkyl hydrazone depicted in Scheme 1 is part of a reagent for the preparation of a radiopharmaceutical, when it undergoes the shown reaction with other aldehydes and ketones it will be decomposed or degraded into one or more other hydrazones depending on the number of aldehydes and ketones with which it comes into contact. These decomposition products constitute impurities in the reagent which must be minimized or avoided. The elimination of all aldehydes and ketones is very difficult in a manufacturing setting because they can be extracted from a number of the materials, particularly plastics and rubber stoppers, used in the manufacturing process and are present in the common disinfectants. The use of stable hydrazones in the novel reagents of the present invention, which are comprised of stable hydrazone modified biologically active molecules, obviates this problem. Thus, the stable hydrazone reagents of this invention enjoy a significant advantage over the lower alkyl protected hydrazones disclosed in the prior art, this due to the increased stability of the stable hydrazone reagents, which renders them capable of commercialization.

The stable hydrazone group, $H_z$, of the formula $-N(R^{40}R^{41})N=C(R^{80}R^{81})$, differs from the lower alkyl hydrazones in that one of the substituents $R^{80}$ and $R^{81}$ is selected from the group: nitrile, carboxylic acids, carboxylic acid esters, carboxamides, 1-alkenes, 1-alkynes, aryl, unsaturated heterocycle, and unsaturated carbocycle; or the two substituents $R^{80}$ and $R^{81}$ are taken together to form a ring system. The substituents in the group serve to stabilize the hydrazone by providing a conjugated π system either as a carbon-carbon double bond, a carbon-oxygen double bond, a carbon-carbon triple bond, a carbon-nitrogen triple bond or an aromatic ring. Stability can also be provided by the chelate effect if the substituents $R^{80}$ and $R^{81}$ are taken together to form a ring system.

The reagents of the present invention can be synthesized by a variety of methods. The hydrazine and hydrazide precursors may be prepared as described in co-pending application U.S. Ser. No. 08/415,908,861. The stable hydrazone group $H_z$ can be introduced at any step in the synthesis of the reagent provided that it is stable to subsequent reaction conditions. One synthetic approach involves the reaction of a stable hydrazone group bearing a coupling functionality with a biologically active molecule, Q, optionally bearing a linking group, $L_n$. A coupling functionality is a chemically reactive moiety capable of reacting with a biologically active molecule, optionally bearing a linking group, to bind the stable hydrazone thereto. For biologically active molecules bearing a linking group, the stable hydrazone is bound to the linking group.

The reaction of the stable hydrazone bearing a chemically reactive moiety with a biologically active molecule or linker modified biologically active molecule can be performed by direct combination of the two reactants in a suitable solvent and under suitable reaction conditions. A solvent or reaction condition is suitable if the stable hydrazone-biologically active molecule or stable hydrazone-linker-biologically active molecule reagent is formed without a significant loss of biological activity due to the use of said solvent or condition.

Examples of chemically reactive moieties include an alkyl group bearing a good leaving group such as a halide, a carbonyl group such as an acid anhydride, acid halide, or active ester, an isothiocyanate or substituted isothiocyanate, or a maleimide. An active ester is an ester that is more reactive in nucleophilic substitution reactions such as tetrafluorophenyl, N-succinimidyl, and nitrophenyl. In the reaction between the stable hydrazone bearing a chemically reactive moiety and a biologically active molecule or linker modified biologically active molecule, either reactant can serve as the nucleophile. More detailed descriptions of these coupling reactions can be found in Brinkley, M., *Bioconjugate Chemistry*, 1992, Vol. 3, No. 1, which is incorporated herein by reference. Also, U.S. Pat. No. 5,206,370, which is incorporated herein, discloses other examples of chemically reactive moieties.

Another synthetic approach involves formation of the stable hydrazone as the last step in the synthesis of the reagent. Compounds of the formula $(Q)_d-L_n-C_h$, in which $C_h$ is $-R^{40}R^{41}NNH_2$, the synthesis of which are described in co-pending U.S. Ser. No. 08/415,908,861, can be reacted with carbonyl-containing compounds of the formula $R^8C(=O)R^{81}$ in a suitable solvent under suitable reaction conditions. A solvent or reaction condition is suitable if the reagent is formed without a significant loss of biological activity due to the use of said solvent or condition.

Stable hydrazones bearing a chemically reactive group useful in the synthesis of the reagents of the present invention can be synthesized as shown in Scheme 2.

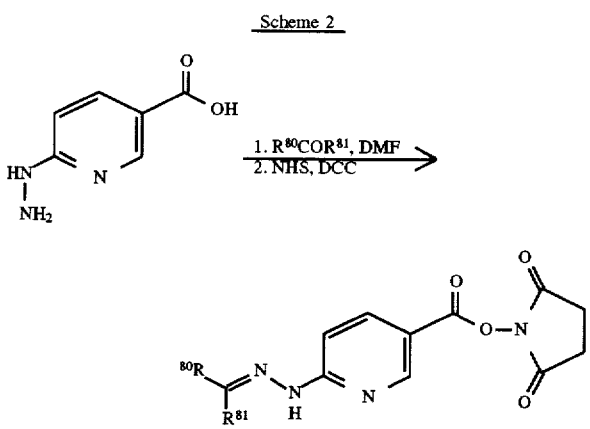

Scheme 2

Hydrazinonicotinic acid is reacted with a carbonyl-containing compound, $R^{80}C(=O)R^{81}$, in dimethylformamide to form the respective stable hydrazone of nicotinic acid. Reaction of the stable hydrazone solution with N-hydroxysuccinimide (NHS) in the presence of dicyclohexylcarbodiimide (DCC) results in the succinimidyl ester of the respective stable hydrazone of nicotinic acid. The syntheses of specific stable hydrazones bearing a succinimidyl ester chemically reactive moiety are described in the Example Section.

The stable hydrazones bearing a succinimidyl ester moiety can be used to prepare reagents of the present invention by reaction with an amino group on a biologically active molecule or linker-modified biologically active molecule to form an amide bond. The synthesis of reagents by reaction with linker modified cyclic IIb/IIIa receptor antagonists is shown in Scheme 3.

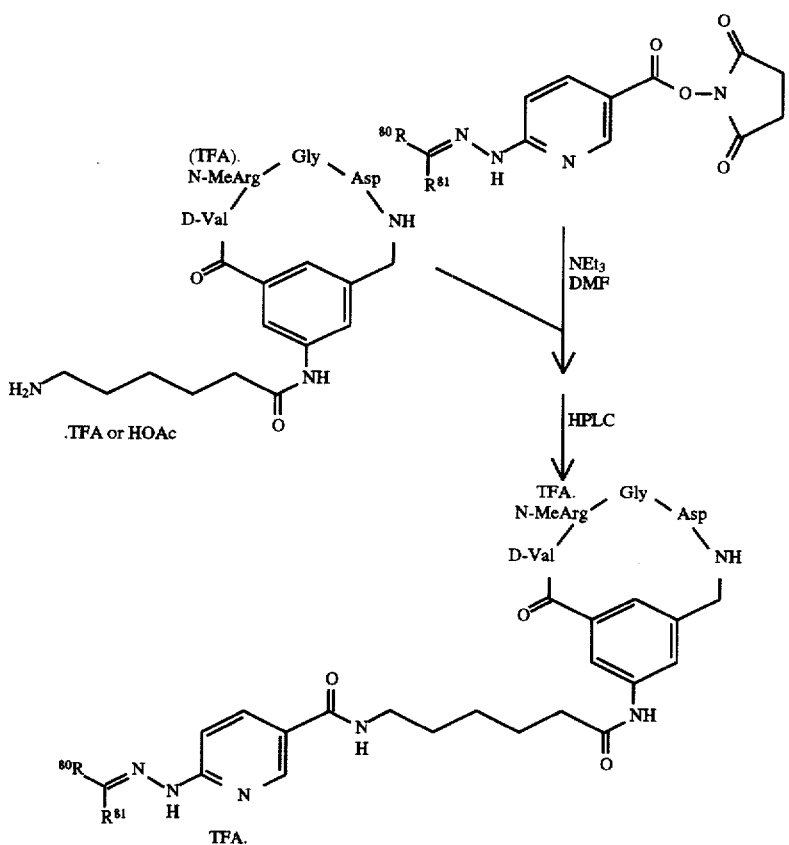

Scheme 3.

A dimethylformamide solution of a hydrazone bearing a succinimidyl ester moiety is combined with the linker modified cyclic IIb/IIIa receptor antagonist cyclo-(D-Val-NMeArg-Gly-Asp-Mamb(5-Aca)) dissolved in DMF to form a reagent, cyclo-(D-Val-NMeArg-Gly-Asp-Mamb(H$_2$-5-Aca)). Cyclo-(D-Val-NMeArg-Gly-Asp-Mamb(5-Aca)) is synthesized as described in copending U.S. Ser. No. 08/415,908,861. The crude reagent can be purified by preparative high performance liquid chromatography (HPLC) or by a number of other methods known to those skilled in the art, such as recrystallization, column chromatography and solvent extraction.

An alternative approach for the synthesis of the reagent of the present invention involves reaction of a carbonyl-containing compound of the formula $R^{80}C(=O)R^{81}$ with a compound of the formula $(Q)_{d'}-L_n-C_{h'}$, wherein $C_h$ is $-R^{40}R^{41}NNH_2$, as shown in Scheme 4.

$$[(Q)_{d'}-L_n-C_{h'}]_x-M_r(A_{L1})_y(A_{L2})_z \quad (2),$$

wherein Q, d', and $L_n$ are as defined above and $C_{h'}$ is a radionuclide metal chelator or bonding unit bound to the transition metal radionuclide, $M_r$, of the formulae $R^{40}N=N^+$ =, $R^{40}R^{41}N-N=$, $R^{40}N=$, or $R^{40}N=N(H)-$, $A_{L1}$ is a first ancillary or co-ligand, $A_{L2}$ is a second ancillary or co-ligand, x and y are independently 1 or 2, and z is independently an integer from 0 to 4. The transition metal radionuclide, $M_r$, can be selected from the group: technetium-99m, rhenium-186 and rhenium-188.

The group $C_{h'}$ is termed a hydrazido (of formula $R^{40}R^{41}N-N=$), diazenido (of formula $R^{40}N=N^+=$ or $R^{40}N=N(H)-$) or imido (of formula $R^{40}N=$) group and serves as the point of attachment of the radionuclide to the remainder of the radiopharmaceutical designated by the formula $(Q)_{d'}-L_n$. A diazenido group can be either terminal (only one atom of the group is bound to the radionuclide) or

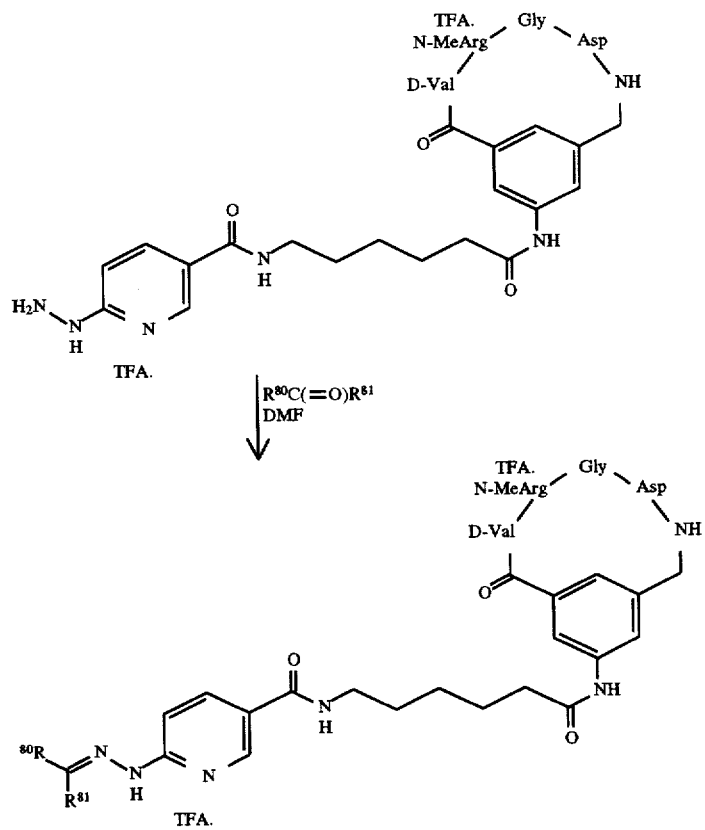

Scheme 4.

The cyclic IIb/IIIA receptor antagonist, cyclo-(D-Val-NMeArg-Gly-Asp-Mamb(Hynic-5-Aca)), which can be synthesized as described in co-pending U.S. Ser. No. 08/415,908,861, is reacted with a carbonyl-containing compound of the formula $R^{80}(C=O)R^{81}$ in dimethylformamide to give a reagent cyclo-(D-Val-NMeArg-Gly-Asp-Mamb (H$_2$-5-Aca)). The crude reagent can be purified by preparative high performance liquid chromatography (HPLC) or by a number of other methods known to those skilled in the art, such as recrystallization, column chromatography and solvent extraction.

The reagents of the present invention of the formula $(Q)_{d'}-L_n-H_z$, are useful for the preparation of radiopharmaceuticals disclosed in copending patent application Ser. No. 08/415,908,908 of formula:

chelating. In order to have a chelating diazenido group at least one other atom of the group, located on $R^{40}$, must also be bound to the radionuclide. The atoms bound to the metal are termed donor atoms. The hydrazido and imido groups are exclusively terminal.

The coordination sphere of the radionuclide includes all the ligands or groups bound to the radionuclide. For a transition metal radionuclide, $M_r$, to be stable it typically has a coordination number comprised of an integer greater than or equal to 5 and less than or equal to 7; that is there are 5 to 7 atoms bound to the metal and it is said to have a complete coordination sphere. If the chelator or bonding unit $C_{h'}$ does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

The radiopharmaceuticals prepared from the reagents of the present invention can be comprised of one or two ancillary or co-ligands, designated $A_{L1}$, in a binary ligand system. The one or two ancillary or co-ligands, $A_{L1}$, comprising the radiopharmaceuticals can be independently selected from the group: dioxygen ligands, functionalized aminocarboxylates and halides; provided that the coordination sphere of the radionuclide is complete.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis (hydroxymethyl)propionic acid, 4,5-dihydroxy-1,3-benzene disulfonate, or substituted or unsubstituted 1,2 or 3,4 hydroxypyridinones, or pharmaceutically acceptable salts thereof.

Functionalized aminocarboxylates include ligands that have a combination of nitrogen and oxygen donor atoms. Examples include but are not limited to: iminodiacetic acid, 2,3 diaminopropionic acid, nitrilotriacetic acid, N,N'-ethylenediamine diacetic acid, N,N,N'-ethylenediamine triacetic acid, hydroxyethylethylenediamine triacetic acid, N,N'-ethylenediamine bis-hydroxyphenylglycine, or the ligands described in Eur. Pat. Appl. 93302712.0, or pharmaceutically acceptable salts thereof.

Halides can be chloride, bromide, fluoride or iodide or pharmaceutically acceptable salts thereof.

Of particular utility are radiopharmaceuticals prepared from the reagents of the present invention comprised of two different types of ancillary or co-ligands, one or two ligands designated the first ancillary or co-ligand or ligands, $A_{L1}$, and independently selected from the group: dioxygen ligands, functionalized aminocarboxylates and halides; and one to four ligands designated the second ancillary or co-ligand or ligands, $A_{L2}$, selected from the group: trisubstituted phosphines, trisubstituted arsines, tetrasubstituted diphosphines and tetrasubstituted diarsines, in a ternary ligand system. We have disclosed in copending U.S. Ser. No. 08/415,908, that radiopharmaceuticals of the formula $[(Q)_d L_n—C_{h'}]_x—M_t(A_{L1})_y(A_{L2})_z$ comprised of one or more ancillary or co-ligands $A_{L2}$ are stable compared to said radiopharmaceuticals that are not comprised of one or more ancillary ligands, $A_{L2}$; that is, they have a minimal number of isomeric forms, the relative ratios of which do not change significantly with time, and that remain substantially intact upon dilution.

The hydrazone group, $H_z$, must be converted to a chelator or bonding unit, $C_h$, that is either a hydrazine group of the formula $R^{40}R^{41}NNH_2$ or a diazine group of formula $R^{40}N=NH$, that may or may not be protonated, in order for the chelator or bonding unit $C_h$ to be formed with the metal radionuclide, $M_r$. The chelator or bonding unit, $C_h$, when bound to the metal radionuclide, $M_r$, is designated $C_{h'}$. The conversion of the hydrazone group, $H_z$, to the chelator or bonding unit, $C_h$, can occur either prior to reaction with the radionuclide, in which case the radionuclide and the ancillary or co-ligand or ligands are combined not with the reagent but with a hydrolyzed form of the reagent bearing the chelator or bonding unit, $C_h$, or in the presence of the radionuclide in which case the reagent itself is combined with the radionuclide and the ancillary or co-ligand or ligands. In the latter case, the pH of the reaction mixture must be neutral or acidic.

Radiopharmaceuticals of the formula $[(Q)_d L_n—C_{h'}]_x—M_t(A_{L1})_y$ can be easily prepared from the reagents of the present invention by admixing a salt of a radionuclide, a reagent of Formula 1, an ancillary ligand $A_{L1}$, and a reducing agent, in an aqueous solution at temperatures from room temperature to 100° C. Alternatively, the radiopharmaceuticals can be prepared by first admixing a salt of a radionuclide, an ancillary ligand $A_{L1}$, and a reducing agent in an aqueous solution at temperatures from room temperature to 100° C. to form an intermediate radionuclide complex with the ancillary ligand $A_{L1}$ then adding a reagent of Formula 1 and reacting further at temperatures from room temperature to 100° C.

Radiopharmaceuticals of the formula $[(Q)_d L_n—C_{h'}]_x—M_t(A_{L1})_y(A_{L2})_z$ can be easily prepared from the reagents of the present invention by admixing a salt of a radionuclide, a reagent of Formula 1, an ancillary ligand $A_{L1}$, an ancillary ligand $A_{L2}$, and optionally a reducing agent, in an aqueous solution at temperatures from room temperature to 100° C. Alternatively, the radiopharmaceuticals can be prepared by first admixing a salt of a radionuclide, an ancillary ligand $A_{L1}$, a reagent of Formula 1, and a reducing agent in an aqueous solution at temperatures from room temperature to 100° C. to form an intermediate radionuclide complex, and then adding an ancillary ligand $A_{L2}$ and reacting further at temperatures from room temperature to 100° C.

The total time of preparation will vary depending on the identity of the radionuclide, the identities and amounts of the reactants and the procedure used for the preparation. The preparations may be complete, resulting in >80% yield of the radiopharmaceutical, in 1 minute or may require more time. If higher purity radiopharmaceuticals are needed or desired, the products can be purified by any of a number of techniques well known to those skilled in the art such as liquid chromatography, solid phase extraction, solvent extraction, dialysis or ultrafiltration.

The use of a reagent of the present invention for the synthesis of a radiopharmaceutical for imaging thrombosis, comprising a stable hydrazone-linker modified-cyclic IIb/IIIa receptor antagonist is shown in Scheme 5. The binary ligand system of the technetium-99m radionuclide is comprised of the diazenido bonding unit $C_{h'}$ and two tricine ancillary ligands, $A_{L1}$. The structure shown is only one of a number of possible isomeric forms of the radiopharmaceutical due to coordination isomerism of the diazenido bonding unit and the two tricine ligands.

Scheme 5.

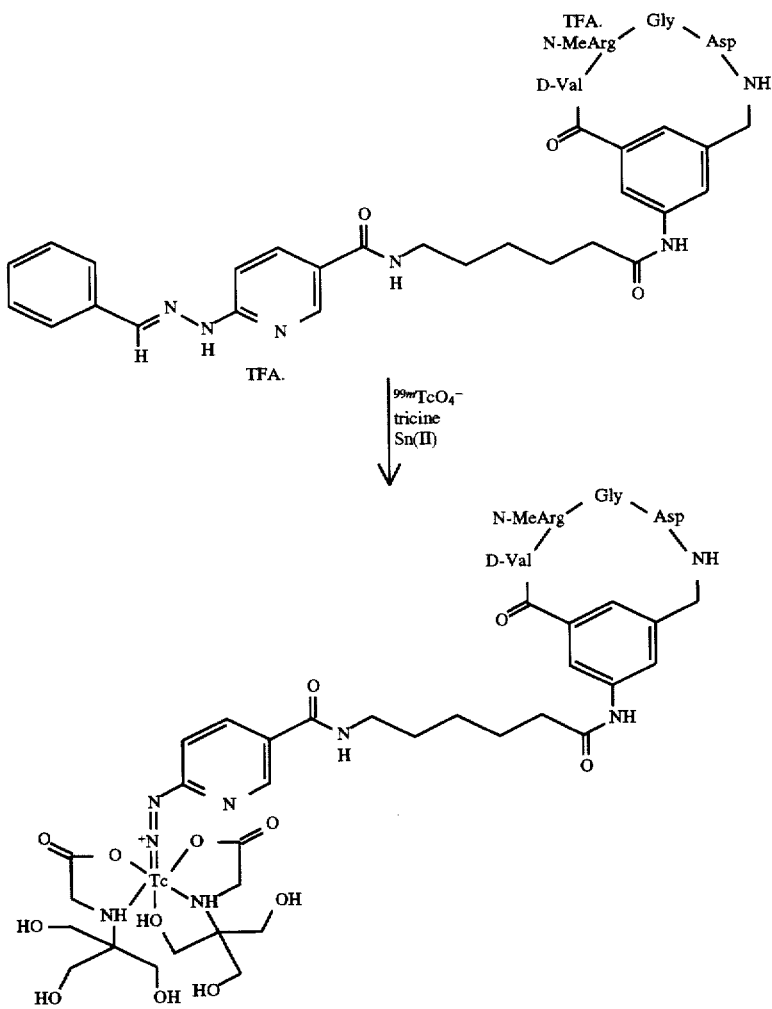

The use of a reagent of the present invention for the synthesis of a radiopharmaceutical for imaging thrombosis, comprising a stable hydrazone-linker modified-cyclic IIb/IIIa receptor antagonist, and having a ternary ligand system, is shown in Scheme 6. The ternary ligand system of the technetium-99m radionuclide is comprised of the diazenido bonding unit $C_{h'}$, one tricine ancillary ligand, $A_{L1}$, and one trisubstituted phosphine ancillary ligand, $A_{L2}$. The structure shown is one of two possible isomeric forms of the radiopharmaceutical due to coordination isomerism of the diazenido bonding unit.

Scheme 6

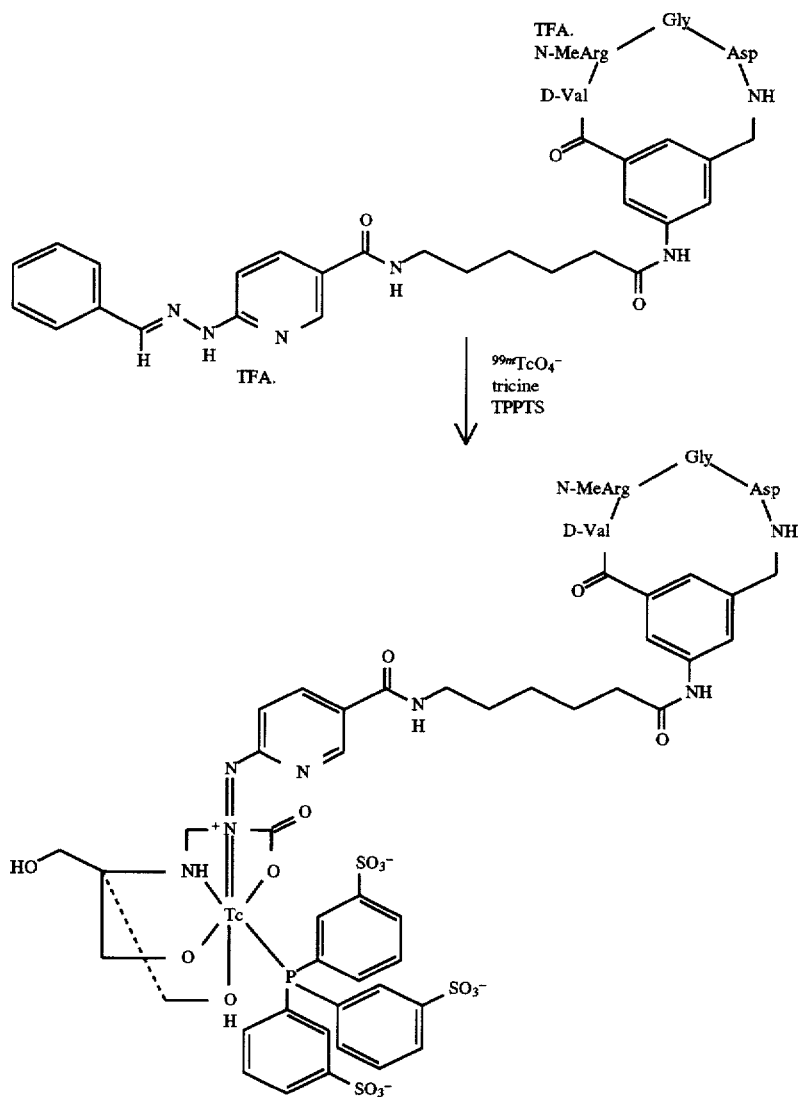

Radionuclides that can used with the reagents of the present invention to synthesize radiopharmaceuticals are selected from the group $^{99m}$Tc, $^{186}$Re, or $^{188}$Re. For diagnostic purposes $^{99m}$Tc is the preferred isotope. Its 6 hour half-life and 140 keV gamma ray emission energy are almost ideal for gamma scintigraphy using equipment and procedures well established for those skilled in the art. The rhenium isotopes also have gamma ray emission energies that are compatible with gamma scintigraphy, however, they also emit high energy beta particles that are more damaging to living tissues. These beta particle emissions can be utilized for therapeutic purposes, for example, cancer radiotherapy.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the reagents of the present invention used to prepare the radiopharmaceuticals can range from 0.1 µg to 10 mg, or more preferably from 0.5 µg to 100 µg. The amount used will be dictated by the amounts of the other reactants and the identity of the radiopharmaceuticals of Formula 2 to be prepared.

The amounts of the ancillary ligands $A_{L1}$ used can range from 0.1 mg to 1 g, or more preferably from 1 mg to 100 mg. The exact amount for a particular radiopharmaceutical is a function of identity of the radiopharmaceuticals of Formula 2 to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as reduced hydrolyzed technetium, or technetium colloid.

The amounts of the ancillary ligands $A_{L2}$ used can range from 0.001 mg to 1 g, or more preferrably from 0.01 mg to 10 mg. The exact amount for a particular radiopharmaceutical is a function of the identity of the radiopharmaceuticals of Formula 2 to be prepared, procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$.

A reducing agent can optionally be used for the synthesis of the radiopharmaceuticals of Formula 2 which are comprised of an ancillary ligand $A_{L2}$. Suitable reducing agents include stannous salts, dithionite or bisulfite salts, borohydride salts, and formamidinesulfinic acid, wherein the salts are of any pharmaceutically acceptable form. The preferred reducing agent is a stannous salt. The use of a reducing agent is optional because the ancillary ligand $A_{L2}$ can also serve to reduce the Tc-99m-pertechnetate. The amount of a reducing agent used can range from 0.001 mg to 10 mg, or more preferably from 0.005 mg to 1 mg.

Another aspect of the present invention are diagnostic kits for the preparation of radiopharmaceuticals useful as imaging agents for the diagnosis of cardiovascular disorders, infectious disease, inflammatory disease and cancer. Diagnostic kits of the present invention comprise one or more vials containing the sterile, non-pyrogenic, formulation comprised of a predetermined amount of the reagent of formula $(Q)_d$—$L_n$—$H_z$, one or two ancillary or co-ligands and optionally other components such as reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practising end user, the ease of manufacturing the kit, the shelf-life of the kit, or the stability and shelf-life of the radiopharmaceutical. The improvement achieved by the inclusion of an optional component in the formulation must be weighed against the added complexity of the formulation and added cost to manufacture the kit. The one or more vials that contain all or part of the formulation can independently be in the form of a sterile solution or a lyophilized solid.

Buffers useful in the preparation of radiopharmaceuticals and in diagnostic kits useful for the preparation of said radiopharmaceuticals include but are not limited to phosphate, citrate, sulfosalicylate, and acetate. A more complete list can be found in the *United States Pharmacopeia*.

Lyophilization aids useful in the preparation diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of said radiopharmaceuticals include but are not limited to ethanol, glycerin, polyethylene glycol, propylene glycol, polysorbates and lecithin.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practising end user can synthesize the radiopharmaceutical and have a high degree of certainty that the radiopharmaceutical can be safely injected into a patient and will provide diagnostic information about the disease state of that patient.

The diagnostic kits of the present invention will also contain written instructions for the practising end user to follow to synthesize the radiopharmaceuticals. These instructions may be affixed to one or more of the vials or to the container in which the vial or vials are packaged for shipping or may be a separate insert, termed the package insert.

Another aspect of the present invention contemplates a method of imaging the site of thrombotic disease in a patient involving: (1) synthesizing a radiopharmaceutical, using a reagent of the present invention, that localizes at the site of the thrombotic disease due to an interaction between the biologically active group, Q, of the radiopharmaceutical and a receptor or binding site expressed at the site of the disease or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of infection or infectious disease in a patient involving: (1) synthesizing a radiopharmaceutical, using a reagent of the present invention, that localizes at the site of the infection or infectious disease due to an interaction between the biologically active group, Q, of the radiopharmaceutical and a receptor or binding site expressed at the site of the disease or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of inflammation in a patient involving: (1) synthesizing a radiopharmaceutical, using a reagent of the present invention, that localizes at the site of the inflammation due to an interaction between the biologically active group, Q, of the radiopharmaceutical and a receptor or binding site expressed at the site of the inflammation or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of cancer in a patient involving: (1) synthesizing a radiopharmaceutical, using a reagent of the present invention, that localizes at the site of the cancer due to an interaction between the biologically active group, Q, of the radiopharmaceutical and a receptor or binding site expressed at the site of the cancer or with a receptor or binding site on an endogenous blood component that accumulates at the site; (2) administering said radiopharmaceutical to a patient by injection or infusion; (3) imaging the patient using either planar or SPECT gamma scintigraphy.

EXAMPLE SECTION

The materials used to synthesize the reagents of the present invention described in the following examples were obtained as follows. Cyclo-(D-Val-NMeArg-Gly-Asp-Mamb(5-Aca)) and cyclo-(D-Val-NMeArg-Gly-Asp-Mamb (Hynic-5-Aca)) was synthesized as described in co-pending U.S. Ser. No. 08/415,908,861 (equivalent to WO 94/22494). The following were obtained from commercial sources and used as received: hydrazinonicotinic acid, N-hydroxysuccinimide (NHS), dicyclohexylcarbodiimide (DCC), tricine, tris(3-sulfonatophenyl)phosphine trisodium salt (TPPTS), stannous chloride dihydrate, dimethylformamide (DMF), trifluoroacetic acid (TFA), acetonitrile, 4-pyridinecarboxaldehyde, ammonium acetate, sodium dihydrogen phosphate, sodium 2-formylbenzenesulfonate, triethylamine, mannitol, crotonaldehye, 4-carboxybenzaldehyde, and glyoxylic acid. Deionized water was obtained from a Milli-Q Water System and was of >18 MΩ quality. Tc-99m-pertechnetate ($^{99m}TcO_4^-$) was obtained from a DuPont Pharma $^{99}Mo/^{99m}Tc$ generator.

Example 1
Synthesis of the Benzaldehyde Hydrazone of Cyclo-(D-Val-NMeArg-Gly-Asp-Mamb(Hydrazinonicotinyl-5-Aca)).

To a solution of 20 mg (0.0215 mmol) of cyclo(D-Val-NMeArg-Gly-Asp-Mamb(5-Aca)).2TFA and 7.5 mg (0.0222 mmol) of succinimidyl 6-(2-benzaldehydehydrazino)nicotinate in DMF (1 ml) was added Et$_3$N (10 µl), and the reaction mixture was allowed to stir at RT for 42 hours. The reaction mixture was concentrated, dissolved in 50% CH$_3$CN/H$_2$O, and lyophilized to provide the crude title compound (23.5 mg) as an off-white powder. Purification was accomplished by reversed-phase HPLC on a preparative Vydac C18 column (2.5×25 cm) using a gradient of 6 to 72% acetonitrile containing 0.1% trifluoroacetic acid at a flow rate of 15 ml/min to give the TFA salt of the title compound (17.5 mg, 71%) as a fluffy white solid; $^1H$ NMR (D$_6$-DMSO) 11.30 (br s, OH), 10.02 (s, NH), 8.94 (d, 1H), 8.61 (d, 1H), 8.55 (d, 1H), 8.41 (m, 2H), 8.10 (s, =CH), 8.09 (m, 1H), 7.70 (m, 4H), 7.61 (m, 1H), 7.52 (t, 1H), 7.42 (m, 3H), 7.27 (d, 1H), 7.07 (s, 1H), 5.18 (dd, 1H), 4.53 (m, 2H), 4.34 (dd, 1H), 4.20 (dd, 1H), 4.02 (dd, 1H), 3.25 (q, 2H), 3.13 (q, 2H), 2.99 (s, NCH$_3$), 2.72 (dd, 1H), 2.50 (m, 1H), 2.33 (t, 2H), 2.10 (m, 2H), 1.60 (m, 5H), 1.35 (m, 4H), 1.10 (d, CH$_3$), 0.92 (d, CH$_3$); FAB(NBA)-MS: [M+H]=926.4625 (Calcd for C$_{45}$H$_{60}$N$_{13}$O$_9$=926.4637).

Example 2
Synthesis of the 2-Formylbenzenesulfonic Acid Hydrazone of Cyclo-(D-Val-NMeArg-Gly-Asp-Mamb (Hydrazinonicotinyl-5-Aca)).

Sodium 2-formylbenzenesulfonate (3.9 mg, 0.019 mmol) and cyclo-(D-Val-NMeArg-Gly-Asp-Mamb (Hydrazinonicotinyl-5-Aca)) (10 mg, 0.0094 mmol) were dissolved in 0.05M sodium phosphate buffer, pH 7.0 (1.0 mL) and allowed to stand at ambient temperature for 1.5 h, at which time the entire reaction had turned to a gel. The gel was dissolved in 1.0 mL of 10% acetonitrile containing 0.1M NH$_4$OAc and purified using reversed-phase HPLC with a preparative Zorbax-RX C18 column (21.2×250 mm) at a flow rate of 15 mL/min using 10% acetonitrile containing 0.1M NH$_4$OAc for two minutes, followed by a 4.44%/min gradient of 10 to 50% acetonitrile containing 1.1M NH$_4$OAc. The product fraction was lyophilized to give the title compound as a fluffy colorless solid (7 mg, 74%). Analytical HPLC with a Zorbax-RX C18 column (4.6×250 mm) at a flow rate of 1.5 mL/min using a 4.0%/min gradient of 10 to 50% acetonitrile containing 0.05M NH$_4$OAc indicated a product purity of 97.3%. DCI-MS: [M+H]=1006.3.

Example 3
Synthesis of the p-Dimethylaminobenzaldehyde Hydrazone of Cyclo-(D-Val-NMeArg-Gly-Asp-Mamb (Hydrazinonicotinyl-5-Aca)).

The title compound was prepared by the general procedure described above for the benzaldehyde hydrazone of cyclo-(D-Val-NMeArg-Gly-Asp-Mamb (Hydrazinonicotinyl-5-Aca)) (Example 1). Coupling of the cyclic compound (32 mg, 0.0344 mmol) and succinimidyl 6-(2-(4-dimethylamino)benzaldehydehydrazino)nicotinate (13.5 mg, 0.0354 mmol) provided the crude title compound (47 mg) as a yellow powder. Purification was accomplished by reversed-phase HPLC on a preparative Vydac C18 column (2.5×25 cm) using a gradient of 9 to 72% acetonitrile containing 0.1% trifluoroacetic acid at a flow rate of 15 ml/min to give the TFA salt of the title compound (29.7 mg, 72%) as a fluffy white solid; $^1H$ NMR (D$_6$-DMSO) 10.03 (s, NH), 8.94 (d, 1H), 8.55 (d, 1H), 8.50 (s, 1H), 8.42 (t, 1H), 8.15 (br s, 1H), 8.06 (s, 1H), 7.70 (d, 2H), 7.61 (m, 4H), 7.16 (d, 1H), 7.07 (s, 1H), 7.00 (br s, 2H), 6.76 (d, 2H), 5.17 (dd, 1H), 4.52 (m, 2H), 4.33 (dd, 1H), 4.20 (dd, 1H), 3.25 (q, 2H), 3.12 (q, 2H), 2.98 (s, 3 NCH$_3$), 2.72 (dd, 1H), 2.50 (m, 1H), 2.33 (t, 2H), 2.10 (m, 2H), 1.60 (m, 5H), 1.35 (m, 4H), 1.10 (d, CH$_3$), 0.92 (d, CH$_3$); FAB(NBA)-MS: [M+H]=969.5043 (Calcd for C$_{47}$H$_{65}$N$_{14}$O$_9$=969.5059).

Example 4
Synthesis of the 4-Carboxybenzaldehyde Hydrazone of Cyclo-(D-Val-NMeArg-Gly-Asp-Mamb (Hydrazinonicotinyl-5-Aca)).

A mixture of cyclo-(D-Val-NMeArg-Gly-Asp-Mamb (Hydrazinonicotinyl-5-Aca)). 2 HBr (50 mg, 50 µmole) and 4-carboxybenzaldehyde (70.35 µmole) was stirred in dimethylformamide (1 mL) at room temperature, under nitrogen, for 4 hours. The solvent was removed under vacuum, the residue dissolved in a mixture of acetonitrile-water, and lyophilized to dryness. The crude mixture was purified by reversed-phase HPLC with a preparative Zorbax-RX C18 column (21.2×250 mm) at a flow rate of 15 mL/min, using a mobile phase of solvent A (50 mM ammonium acetate), solvent B (50 mM ammonium acetate in 50% acetonitrile) and the following gradient: The following gradient was used: 0–2 min, 20% B; 30 min, 50% B (held until 32 min); 35 min, 100% B(held until 38 min); 40 min, 20% B. Yield of purified product 7 mg (14%). DCI-MS (High Resolution) [M+H]=970.453526 (calculated molecular weight 969.445702.

Example 5
Synthesis of the Crotonaldehyde Hydrazone of Cyclo-(D-Val-NMeArg-Gly-Asp-Mamb(Hydrazinonicotinyl-5-Aca))

The title compound was synthesized as described for the 4-carboxybenzaldehyde hydrazone of cyclo-(D-Val-NMeArg-Gly-Asp-Mamb(Hydrazinonicotinyl-5-Aca)) (Example 4) substituting crotonaldehyde for 4-carboxybenzaldehyde. The crude material was purified by preparative HPLC using the following gradient: 0–2 min, 20% B; 4 min, 55% B (held until 5 min); 30 min, 70% B(held until 32 min); 35 min, 100% B (held until 38 min); 40 min, 20% B; to give 4.5 mg (10%) of the purified product. DCI-MS (High Resolution) [M+H]=890.463696 (calculated molecular weight 889.455872.

Example 6
Synthesis of the Glyoxylic Acid Hydrazone of Cyclo-(D-Val-NMeArg-Gly-Asp-Mamb(Hydrazinonicotinyl-5-Aca)).

The title compound was synthesized as described for the 4-carboxybenzaldehyde hydrazone of cyclo-(D-Val-NMeArg-Gly-Asp-Mamb(Hydrazinonicotinyl-5-Aca)) (Example 4) substituting glyoxylic acid for 4-carboxybenzaldehyde. The crude material was purified by preparative HPLC using the following gradient: 0–5 min, 20% B; 40 min, 50% B (held until 42 min); 45 min, 100% B(held until 46 min); 48 min, 20% B to give 4.6 mg (10%) of the purified product. DCI-MS (High Resolution) |M+H| =894.422225 (calculated molecular weight 893.414402.

Example 7
Synthesis of the Acetophenone Hydrazone of Cyclo-(D-Val-NMeArg-Gly-Asp-Mamb(Hydrazinonicotinyl-5-Aca)).

To a solution of 82 mg (0.1075 mmol) of crude cyclo-(D-Val-NMeArg-Gly-Asp-Mamb(5-Aca)).HOAc, TFA (16.6 μl, 0.215 mmol), and 38 mg (0.1075 mmol) of succinimidyl 6-(2-acetophenonehydrazino)nicotinate in DMF (5 ml) was added Et$_3$N (75 μl), and the reaction mixture was allowed to stir at RT for 42 hours. The reaction mixture was concentrated, dissolved in 50% CH$_3$CN/H$_2$O, and lyophilized to provide the crude title compound (130 mg) as a pale yellow powder. Purification of a portion of this material was accomplished by reversed-phase HPLC on a preparative Vydac C18 column (2.5×25 cm) using a gradient of 2 to 90% acetonitrile containing 0.1% trifluoroacetic acid at a flow rate of 15 ml/min to give the TFA salt of the title compound as a fluffy white solid; $^1$H NMR (D$_6$-DMSO) 10.03 (s, NH), 8.93 (d, 1H), 8.62 (s, 1H), 8.55 (d, 1H), 8.42 (m, 2H), 8.13 (br s, 1H), 7.87 (d, 2H), 7.70 (m, 2H), 7.55 (m, 2H), 7.40 (m, 4H), 7.07 (s, 1H), 5.17 (dd, 1H), 4.52 (m, 2H), 4.33 (dd, 1H), 4.20 (dd, 1H), 4.02 (dd, 1H), 3.63 (dd, 1H), 3.26 (q, 2H), 3.12 (q, 2H), 2.98 (s, NCH$_3$), 2.72 (dd, 1H), 2.50 (m, 1H), 2.35 (s, CH$_3$), 2.33 (m, 2H), 2.10 (m, 2H), 1.60 (m, 5H), 1.35 (m, 4H), 1.10 (d, CH$_3$), 0.92 (d, CH$_3$); FAB(NBA)-MS: [M+H]=940.4818 (Calcd for C$_{46}$H$_{62}$N$_{13}$O$_9$=940.4793).

Example 8
Synthesis of the 1-(Methoxycarbonyl)acetaldehyde Hydrazone of Cyclo-(D-Val-NMeArg-Gly-Asp-Mamb(Hydrazinonicotinyl-5-Aca)).

The title compound was prepared by the general procedure described above for the acetophenone cyclo-(D-Val-NMeArg-Gly-Asp-Mamb(Hydrazinonicotinyl-5-Aca)) hydrazone (Example 7). Coupling of the crude cyclic compound (82 mg, 0.1075 mmol) and succinimidyl 6-(2-(1-methoxycarbonyl)acetaldehydehydrazino)nicotinate (36 mg, 0.1077 mmol) provided the crude title compound (123 mg) as a pale yellow powder. Purification of a portion of this material was accomplished by reversed-phase HPLC using the conditions described in Example 8 to give the TFA salt of the title compound as a fluffy white solid; $^1$H NMR (D$_6$-DMSO) 10.69 (s, NH), 10.02 (s, NH), 8.92 (d, 1H), 8.70 (d, 1H), 8.55 (d, 1H), 8.44 (m, 2H), 8.14 (dd, 1H), 7.70 (s, 2H), 7.56 (m, 2H), 7.28 (d, 1H), 7.07 (s, 1H), 5.17 (dd, 1H), 4.52 (m, 2H), 4.33 (dd, 1H), 4.19 (dd, 1H), 4.04 (m, 1H), 3.76 (s, OCH$_3$), 3.63 (dd, 1H), 3.26 (q, 2H), 3.13 (q, 2H), 2.99 (s, NCH$_3$), 2.72 (dd, 1H), 2.50 (m, 1H), 2.33 (t, 2H), 2.13 (s, CH$_3$), 1.60 (m, 5H), 1.35 (m, 4H), 1.10 (d, CH$_3$), 0.92 (d, CH$_3$); FAB-MS: [M+H]=922.4539 (Calcd for C$_{42}$H$_{60}$N$_{13}$O$_{11}$=922.4535).

Example 9
Synthesis of the Cyclopentanone Hydrazone of Cyclo-(D-Val-NMeArg-Gly-Asp-Mamb(Hydrazinonicotinyl-5-Aca)).

The title compound was prepared by the general procedure described above for the acetophenone cyclo-(D-Val-NMeArg-Gly-Asp-Mamb(Hydrazinonicotinyl-5-Aca)) hydrazone (Example 7). Coupling of the crude cyclic compound (82 mg, 0.1075 mmol) and succinimidyl 6-(2-cyclopentanonehydrazino)nicotinate (35 mg, 0.1106 mmol) provided the crude title compound (131 mg) as a pale yellow powder. Purification of a portion of this material was accomplished by reversed-phase HPLC using the conditions described in Example 8 to give the TFA salt of the title compound as a fluffy white solid; $^1$H NMR (D$_6$-DMSO) 10.02 (s, NH), 8.93 (d, 1H), 8.61 (d, 1H), 8.55 (d, 1H), 8.51 (s, 1H), 8.41 (t, 1H), 8.10 (m, 1H), 7.70 (s, 2H), 7.55 (m, 1H), 7.52 (t, 1H), 7.10 (br s, 3H), 7.06 (s, 1H), 5.17 (dd, 1H), 4.52 (m, 2H), 4.33 (dd, 1H), 4.19 (dd, 1H), 4.02 (dd, 1H), 3.62 (d, 1H), 3.24 (q, 2H), 3.12 (q, 2H), 2.99 (s, NCH$_3$), 2.72 (dd, 1H), 2.50 (m, 1H), 2.41 (m, 4H), 2.33 (t, 2H), 2.10 (m, 2H), 1.75 (m, 3H), 1.68 (m, 4H), 1.34 (m, 4H), 1.10 (d, CH$_3$), 0.92 (d, CH$_3$); FAB(NBA/TFA)-MS: [M+H]=904.5136 (Calcd for C$_{43}$H$_{62}$N$_{13}$O$_9$=904.4793).

Example 10
Synthesis of the 2-(Methoxycarbonyl)cyclopentanone Hydrazone of Cyclo-(D-Val-NMeArg-Gly-Asp-Mamb (Hynic-5-Aca))

The title compound was prepared by the general procedure described above for the acetophenone cyclo-(D-Val-NMeArg-Gly-Asp-Mamb(Hydrazinonicotinyl-5-Aca)) hydrazone (Example 7). Coupling of the crude cyclic compound (82 mg, 0.1075 mmol) and succinimidyl 6-(2-(2-methoxycarbonyl)cyclopentanonehydrazino)nicotinate (41 mg, 0.1095 mmol) provided the crude title compound (138 mg) as a pale yellow powder. Purification of a portion of this material was accomplished by reversed-phase HPLC using the conditions described in Example 8 to give the TFA salt of the title compound as a fluffy white solid; $^1$H NMR (D$_6$-DMSO) 10.01 (s, NH), 8.90 (m, 1H), 8.57 (m, 2H), 8.39 (m, 2H), 8.07 (d, 1H), 7.71 (s, 2H), 7.59 (m, 2H), 7.09 (m, 2H), 5.17 (dd, 1H), 4.52 (m, 2H), 4.34 (dd, 1H), 4.20 (dd, 1H), 4.02 (d, 1H), 3.67 (S, OCH$_3$), 3.24 (q, 2H), 3.12 (m, 2H), 2.99 (s, NCH$_3$), 2.71 (dd, 1H), 2.50 (m, 1H), 2.34 (t, 2H), 2.10 (m, 4H), 1.60 (m, 5H), 1.34 (m, 3H), 1.25 (m, 2H), 1.10 (d, CH$_3$), 0.93 (d, CH$_3$); ESI-MS: [M+H]=962 (Calcd for C$_{45}$H$_{64}$N$_{13}$O$_{11}$=962.4848).

Example 11
Synthesis of the 4-Pyridinecarboxaldehyde Hydrazone of Cyclo-(D-Val-NMeArg-Gly-Asp-Mamb (Hydrazinonicotinyl-5-Aca)).

4-Pyridinecarboxaldehyde (1.14 mg, 0.0106 mmol) and cyclo-(D-Val-NMeArg-Gly-Asp-Mamb(Hynic-5-Aca)) (10 mg, 0.0094 mmol) were dissolved in 0.05M sodium phosphate buffer, pH 7.0 (5.0 mL) and allowed to stand at ambient temperature for 72 h. The now slightly yellow solution was lyophilized to dryness and the resulting solid was purified using reversed-phase HPLC with a preparative Zorbax-RX C18 column (21.2×250 mm) at a flow rate of 15 mL/min using 10% acetonitrile containing 0.1M NH$_4$OAc for two minutes, followed by a 4.44%/min gradient of 10 to 50% acetonitrile containing 0.1M NH$_4$OAc. The product fraction (retention time 10–12 min) was lyophilized to give the title compound as a fluffy colorless solid (8 mg, 74%). Analytical HPLC with a Zorbax-RX C18 column (4.6×250 mm) at a flow rate of 1.5 mL/min using a 4.0%/min gradient of 10 to 50% acetonitrile containing 0.05M NH$_4$OAc indicated a product purity of 98.7%.

The following examples illustrate the synthesis of stable hydrazones bearing a chemically reactive moiety useful in the synthesis of the reagents described above.

Example 12
Synthesis of Succinimidyl 6-(2-Benzaldehydehydrazino) nicotinate

To a suspension of 6-hydrazinonicotinic acid (1.00 g, 6.5 mmol) in DMF (40 ml) was added benzaldehyde (0.70 ml, 6.9 mmol), and the reaction mixture was allowed to stir at room temperature for 3 hours. To the homogeneous reaction mixture was added N-hydroxysuccinimide (752 mg, 6.5 mmol) and DCC (3.00 ml, 13.4 mmol), and the reaction mixture was allowed to stir at room temperature for 18 hours. The reaction mixture was filtered, concentrated, diluted with EtOAc (50 ml), and the mixture was heated at reflux for 1 hour. Filtration of the hot mixture provided the title compound (1.78 g, 81%) as a pale yellow powder. This material was used without further purification. $^1$H NMR ($D_6$-DMSO) 11.86 (s, NH), 8.82 (dd, Py-H), 8.20 (dd, Py-H), 8.20 (s, =CH), 7.75 (dd, 2 Ar-H), 7.43 (m, Py-H & 3 Ar-H), 2.89 (s, 2 $CH_2$); DCI($NH_3$)-MS: [M+H]=339.1084 (Calcd for $C_{17}H_{15}N_4O_4$=339.1093).

Example 13
Synthesis of Succinimidyl 6-(2-Acetophenonehydrazino) nicotinate

The title compound was prepared by the general procedure described above for succinimidyl 6-(2-benzaldehydehydrazino)nicotinate (Example 12). Filtration of the EtOAc mixture provided the title compound (1.26 g, 55%, contains traces of DCU) as an off-white powder. A pure sample of the title compound (853 mg, 37%) was obtained from the filtrate as golden crystals. $^1$H NMR ($D_6$-DMSO) 10.86 (s, NH), 8.84 (dd, Py-H), 8.21 (dd, Py-H), 7.86 (dd, 2 Ar-H), 7.41 (m, Py-H & 3 Ar-H), 2.89 (s, 2 $CH_2$), 2.39 (s, $CH_3$); DCI($NH_3$)-MS: [M+H]=(Calcd for $C_{18}H_{17}N_4O_4$=353.1250).

Example 14
Synthesis of Succinimidyl 6-(2-(4-Dimethylamino) benzaldehydehydrazino)nicotinate The title compound was prepared by the general procedure described above for succinimidyl 6-(2-benzaldehydehydrazino)nicotinate (Example 12), except that only 1 equivalent of DCC (1.5 ml, 6.7 mmol) was used. Hot filtration of the EtOAc mixture provided the title compound (1.20 g, 48%) as a yellow powder. This material was used without further purification. $^1$H NMR ($D_6$-DMSO) 11.58 (s, NH), 8.76 (dd, Py-H), 8.13 (dd, Py-H), 8.07 (s, =CH), 7.54 (d, 2 Ar-H), 7.29 (d, Py-H), 6.75 (d, 2 Ar-H), 2.97 (s, 2 $NCH_3$), 2.88 (s, 2 $CH_2$); DCI($NH_3$)-MS: [M+H]=382.1513 (Calcd for $C_{19}H_{20}N_5O_4$=382.1515).

Example 15
Synthesis of Succinimidyl 6-(2-(1-Methoxycarbonyl) acetaldehydehydrazino)nicotinate The title compound was prepared by the general procedure described above for succinimidyl 6-(2-benzaldehydehydrazino)nicotinate (Example 12). Filtration of the EtOAc mixture provided the title compound (552 mg, 25%, contains traces of DCU) as a pale white powder. This material was used without further purification. Concentration of the filtrate, and trituration with EtOAc provided the title compound (349 mg, 16%, contains traces of DCU). $^1$H NMR ($D_6$-DMSO) 11.21 (s, NH), 8.91 (dd, Py-H), 8.33 (dd, Py-H), 7.42 (d, Py-H), 3.78 (s, $OCH_3$), 2.89 (s, 2 $CH_2$), 2.18 (s, $CH_3$); DCI($NH_3$)-MS: [M+H]=(Calcd for $C_{14}H_{15}N_4O_6$=335.0991).

Example 16
Synthesis of Succinimidyl 6-(2-Cyclopentanonehydrazino) nicotinate

The title compound was prepared by the general procedure described above for succinimidyl 6-(2-benzaldehydehydrazino)nicotinate (Example 12). Filtration of the EtOAc mixture provided the title compound (1.78 g, 86%, contains traces of DCU) as a pale yellow powder. Recrystallization of this material from EtOAc provided a purified sample of the title compound (530 mg, contains traces of DCU). This material was used without further purification. $^1$H NMR ($D_6$-DMSO) 10.33 (s, NH), 8.76 (dd, Py-H), 8.11 (dd, Py-H), 7.15 (d, Py-H), 2.88 (s, 2 $CH_2$), 2.41 (q, 2 $CH_2$), 1.75 (m, 2 $CH_2$); DCI($NH_3$)-MS: [M+H]=(Calcd for $C_{15}H_{17}N_4O_4$=317.1250).

Example 17
Synthesis of Succinimidyl 6-(2-(2-Methoxycarbonyl) cyclopentanonehydrazino)nicotinate The title compound was prepared by the general procedure described above for succinimidyl 6-(2-benzaldehydehydrazino)nicotinate (Example 12). Filtration of the EtOAc mixture provided the title compound (627 mg, 26%, contains traces of DCU) as an off-white powder. Concentration of the filtrate, and trituration with EtOAc provided the title compound (1.17 g, 48%, contains traces of DCU). This material was used without further purification. $^1$H NMR ($D_6$-DMSO) 10.56 (s, NH), 8.79 (dd, Py-H), 8.15 (dd, Py-H), 7.11 (d, Py-H), 3.67 (s, $OCH_3$), 3.55 (t, CH), 2.88 (s, 2 $CH_2$), 2.50 (m, $CH_2$), 1.90 (m, 2 $CH_2$); DCI($NH_3$)-MS: [M+H]=(Calcd for $C_{17}H_{19}N_4O_6$=375.1304).

Example 18
Synthesis of Succinimidyl 6-(2-(2-Sulfo) benzaldehydehydrazino)nicotinate Sodium Salt The title compound was prepared by the general procedure described above for succinimidyl 6-(2-benzaldehydehydrazino)nicotinate (Example 12). Filtration of the EtOAc mixture provided a yellow solid, half of this material was diluted with EtOAc (50 ml), and the mixture was heated at reflux for 1 hour. Filtration of the hot mixture provided the title compound (1.63 g, 85%) as a pale yellow powder. This material was used without further purification. $^1$H NMR ($D_6$-DMSO) 11.91 (s, NH), 9.16 (s, =CH), 8.79 (dd, Py-H), 8.16 (dd, Py-H), 8.03 (dd, Ar-H), 7.79 (dd, Ar-H), 7.35 (m, Py-H & 2 Ar-H), 2.88 (s, 2 $CH_2$); FAB (NBA)-MS: [M+H]=419.2240 (Calcd for $C_{17}H_{15}N_4O_7S$= 419.0661); Anal. Calcd for $C_{17}H_{14}NaN_4O_7S\cdot(H_2O)_{1.5}$: C, 43.69; H, 3.45; N, 11.99; Na, 4.92; S, 6.86. Found: C, 43.62, 43.71; H, 3.59, 3.64; N, 12.13, 12.08; Na, 4.83, 4.67; S, 6.56, 6.30.

Hydrazone Stability Testing

The stability of the reagents of the present invention were tested by combining a solution of the reagents and a solution of formaldehyde and monitoring the mixture by HPLC using Method 1.

| HPLC Method 1: | |
| --- | --- |
| Column: | Zorbax Rx C18 (4.6 mm × 25 cm) |
| Column Temp.: | 50° C. |
| Flow Rate: | 1.5 mL/min |
| Solvent A: | 50 mM ammonium acetate |
| Solvent B: | 50/50 50 mM ammonium acetate:acetonitrile |
| Gradient: t = 0 | 20% B |
| t = 20 min | 100% B |
| t = 22 min | 100% B |
| t = 23 min | 20% B |
| Wavelength: | 240 nm |

The reagent of Example 1 was dissolved in 0.05M phosphate buffer, pH 7, (0.1 mg/mL) and 10 equivalents of formaldehyde (0.1 M in phosphate buffer) added. The reaction mixture was analyzed every 0.5 h by HPLC. The change in peak area for the reagent of Example 1, expressed as a percentage of the initial value prior to formaldehyde addition, is shown in FIGURE 1. For comparison, the lower alkyl hydrazone, cyclo-(D-Val-NMeArg-Gly-Asp-Mamb (hydrazino-nicotinyl-5-Aca)) propionaldehyde hydrazone was also tested. The reagent of Example 1 does not react with formaldehyde over 2.5 h whereas >90% of the lower alkyl hydrazone reacts over 2 h.

In addition, a number of the reagents were generated in situ by reaction of 1 equivalent of the respective aldehyde or ketone with Cyclo(D-Val-NMeArg-Gly-Asp-Mamb (hydrazinonicotinyl-5-Aca)) in 0.05M phosphate buffer, pH 7.0 (0.1 mg/mL) and then their stability tested by addition of one equivalent of formaldehyde and monitoring the solution by HPLC. The stability test results are shown in Table 1.

TABLE 1

Formaldehyde Stability of Reagents

| Example | Formaldehyde Test % Decrease* |
|---|---|
| 1 | 0 |
| 2 | 0 |
| 3 | 0 |
| 4 | 0 |
| 5 | 0 |
| 6 | <1 |
| 9 | 0 |
| 11 | 0 |
| phenylacetaldehyde | 25 |
| glycolaldehyde | 40 |
| Lower Alkyl | 77 |

*at 2 h

The amounts of the reagents of Examples 1–6, 9 and 11 decrease <1% over 2 h of exposure to one equivalent of formaldehyde indicating that they are very stable. In contrast, the amount of the lower alkyl hydrazone, cyclo-(D-Val-NMeArg-Gly-Asp-Mamb(hydrazino-nicotinyl-5-Aca)) propionaldehyde hydrazone, designated Lower Alkyl, decreases by 77% under the same conditions. Also included in Table 1 are the results for two other hydrazones, cyclo-(D-Val-NMeArg-Gly-Asp-Mamb(hydrazinonicotinyl-5-Aca)) phenylacetaldehyde hydrazone, designated phenylacetaldehyde, and cyclo-(D-Val-NMeArg-Gly-Asp-Mamb(hydrazinonicotinyl-5-Aca)) glycolaldehyde hydrazone, designated glycolaldehyde, the structures of which are not circumscribed by this invention. The phenylacetaldehyde hydrazone, in which there is a benzyl group attached to the methylene carbon atom of the hydrazone, shows somewhat better stability, decreasing by 25%, while the glycolaldehyde hydrazone, in which there is a hydroxymethyl group attached to the methylene carbon atom of the hydrazone, shows marginally improved stability, decreasing by 40%. These data show that for a hydrazone to be very stable, as are the reagents of the present invention, there must either be a conjugated π-system or the hydrazone must be part of a ring system. The phenyl group of the phenylacetaldehyde hydrazone is not conjugated to the C=N bond because it is one carbon atom removed. The glycolaldehyde hydrazone does not contain another π-system.

The synthesis of a radiopharmaceutical of Formula 2 useful as a thrombus imaging agent from the reagents described in the preceeding examples can be performed as described below.

Radiolabeling of Reagents Using Stannous Chloride

To a 10 mL vial was added 0.4 mL of tricine solution (40 mg) in $H_2O$, followed by 0.2 mL of reagent solution in $H_2O$ (10–20 µg), 0.5 mL of $^{99m}TcO_4^-$ solution (~50 mCi), 0.2 mL of TPPTS solution (1 mg) in $H_2O$ and 20 µl of $SnCl_2 \cdot 2H_2O$ solution (20 µg in 0.1N HCl). The pH of the solution was adjusted to 4 if necessary. The reaction mixture was heated at 50°–80° C. for 30 min, and was analyzed by radio-HPLC using Method 2 or 3.

Radiolabeling of Reagents without Stannous Chloride

To a 10 mL vial was added 0.1 mL tricine solution (10 mg) in $H_2O$, 0.4 mL reagent solution (20–40 µg) in $H_2O$, 0.5 mL $^{99m}TcO_4^-$ (~50 mCi) in saline, 0.2 mL mannitol solution (20 mg) in $H_2O$, and 0.20 mL TPPTS solution (7.0 mg) in $H_2O$. The pH was adjusted to 4 using 0.1N HCl. The reaction mixture was heated at 50°–80° C. for 30 min and then analyzed by radio-HPLC using Method 2 or 3.

HPLC Method 2

Column: Vydac $C_{18}$, 250 mm × 4.6 mm, 300 Å pore size
Solvent A: 10 mM sodium monophosphate, pH 6.0
Solvent B: 100% acetonitrile
Gradient:

| 0% B | 30% B | 75% B | 0% B |
|---|---|---|---|
| 0' | 15' | 25' | 30' |

Flow: 1.0 mL/min
Detection by NaI probe

HPLC Method 3

Column: Vydac $C_{18}$, 250 mm × 4.6 mm, 300 Å pore size
Solvent A: 10 mM sodium monophosphate, pH 6.0
Solvent B: 100% acetonitrile
Column Temperature 50° C.
Gradient:

| 5% B | 13% B | 20% B | 75% B | 5% B |
|---|---|---|---|---|
| 0' | 15' | 20' | 25' | 30' |

Flow: 1.0 mL/min
Detection by NaI probe

The radiopharmaceutical, $^{99m}Tc(tricine)(TPPTS)(cyclo$ (D-Val-NMeArg-Gly-Asp-Mamb(hydrazinonicotinyl-5-Aca)), formed is identical to that described in Example 1 of copending U.S. Ser. No. 08/415,908, synthesized from the non-hydrazone reagent Cyclo(D-Val-NMeArg-Gly-Asp-Mamb(hydrazinonicotinyl-5-Aca), the synthesis of which is described in co-pending U.S. Ser. No. 08/415,908,861, that was demonstrated to have utility as a thrombus imaging agent. The radiopharmaceutical is formed in >80% yield (based on Tc-99m) using the reagents described in Examples 1–6 and 8.

TABLE 2

Radiopharmaceutical Yields Using Reagents

| Example | RCF % |
|---|---|
| 1 | 94 |
| 2 | 91 |
| 3 | 86* |
| 4 | 87 |
| 5 | 83 |
| 6 | 91* |
| 7 | 45 |

49

TABLE 2-continued

Radiopharmaceutical Yields Using Reagents

| Example | RCF % |
|---|---|
| 8 | 87 |
| 11 | 30* |

*heated at 50° C.

The fact that the radiopharmaceutical can be formed in good yield from the reagents of the present invention is a surprising result since the reagents have been demonstrated to be very stable and yet they must be hydrolyzed in situ for the radiopharmaceutical to be formed. The reagents of the present invention do not react with the aldehydes and ketones that are frequently encountered in a pharmaceutical manufacturing setting, such as used in the manufacture of diagnostic kits, and thus maintain their purity during the manufacturing process in marked contrast to reagents comprised of lower alkyl hydrazones.

We claim:

1. A reagent having the formula:

$$(Q)_{d'}L_n-H_z,$$

and pharmaceutically acceptable salts thereof wherein,

Q is a biologically active group selected from the group: peptides, polypeptides, and peptidomimetics;

d' is 1–20;

$L_n$ is a linking group of formula:

$$M^1-[Y^1(CR^{55}R^{56})_g Y^2]_f-M^2,$$

wherein:

$M^1$ is $-[(CH_2)_gZ^1]_{g'}-(CR^{55}R^{56})_{g''}-$;
$M^2$ is $-(CR^{55}R^{56})_{g''}-[Z^1(CH_2)_g]_{g'}-$;
g is independently 0–10;
g' is independently 0–1;
g" is independently 0–10;
f is independently 0–10;
f' is independently 0–10;
f" is independently 0–1;

$Y^1$ and $Y^2$, are independently selected at each occurrence from: a bond, O, $NR^{56}$, C=O, C(=O)O, OC(=O)O, C(=O)NH—, C=$NR^{56}$, S, SO, $SO_2$, $SO_3$, NHC(=O), $(NH)_2C$(=O), $(NH)_2C$=S;

$Z^1$ is independently selected at each occurrence from a $C_6-C_{14}$ saturated, partially saturated, or aromatic carbocyclic ring system, substituted with 0–4 $R^{57}$; and a heterocyclic ring system, substituted with 0–4 $R^{57}$;

$R^{55}$ and $R^{56}$ are independently selected at each occurrence from: hydrogen; $C_1-C_{10}$ alkyl substituted with 0–5 $R^{57}$; alkaryl wherein the aryl is substituted with 0–5 $R^{57}$;

$R^{57}$ is independently selected at each occurrence from the group: hydrogen, OH, $NHR^{58}$, C(=O) $R^{58}$, OC(=O)$R^{58}$, OC(=O)O$R^{58}$, C(=O)O$R^{58}$, C(=O)N$R^{58}$, C=N, S$R^{58}$, SO$R^{58}$, $SO_2R^{58}$, NHC (=O)$R^{58}$, NHC(=O)NH$R^{58}$, NHC(=S)NH$R^{58}$; or, alternatively, when attached to an additional molecule Q, $R^{57}$ is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C$(=O), $(NH)_2$C=S; and,

50

$R^{58}$ is independently selected at each occurrence from the group: hydrogen; $C_1-C_6$ alkyl; benzyl, and phenyl;

$H_z$ is a stable hydrazone of formula:

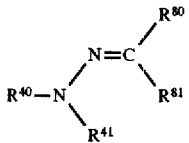

wherein, $R^{40}$ is independently selected at each occurrence from the group: a bond to $L_n$, $C_1-C_{10}$ alkyl substituted with 0–3 $R^{52}$, aryl substituted with 0–3 $R^{52}$, cycloalkyl substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52}$;

$R^{41}$ is independently selected from the group: hydrogen, aryl substituted with 0–3 $R^{52}$, $C_1-C_{10}$ alkyl substituted with 0–3 $R^{52}$, and a heterocycle substituted with 0–3 $R^{52}$;

$R^{52}$ is independently selected at each occurrence from the group: a bond to $L_n$, =O, F, Cl, Br, I, —CF$_3$, —CN, —CO$_2R^{53}$, —C(=O)$R^{53}$, —C(=O)N($R^{53}$)$_2$, —CHO, —CH$_2$O$R^{53}$, —OC(=O)$R^{53}$, —OC(=O) O$R^{53a}$, —O$R^{53}$, —OC(=O)N($R^{53}$)$_2$, —N$R^{53}$C (=O) $R^{53}$, —N$R^{54}$C(=O)O$R^{53a}$, —N$R^{53}$C(=O) N($R^{53}$)$_2$, —N$R^{54}$SO$_2$N($R^{53}$)$_2$, —N$R^{54}$SO$_2R^{53a}$, —SO$_3$H, —SO$_2R^{53a}$, —S$R^{53}$, —S(=O)$R^{53a}$, —SO$_2$N($R^{53}$)$_2$, —N($R^{53}$)$_2$, —NHC(=NH)NH$R^{53}$, —C(=NH)NH$R^{53}$, =NO$R^{53}$, NO$_2$, —C(=O) NHO$R^{53}$, —C (=O)NHN$R^{53}R^{53a}$, —OCH$_2$CO$_2$H, 2-(1-morpholino)ethoxy;

$R^{53}$, $R^{53a}$, and $R^{54}$ are each independently selected at each occurrence from the group: hydrogen, $C_1-C_6$ alkyl, and a bond to $L_n$;

$R^{80}$ and $R^{81}$ are independently selected from the group: H; $C_1-C_{10}$ alkyl; —CN; —CO$_2R^{85}$; —C(=O)$R^{85}$; —C(=O)N($R^{85}$)$_2$; $C_2-C_{10}$ 1-alkene substituted with 0–3 $R^{84}$; $C_2-C_{10}$ 1-alkyne substituted with 0–3 $R^{84}$; aryl substituted with 0–3 $R^{84}$; unsaturated heterocycle substituted with 0–3 $R^{84}$; and unsaturated carbocycle substituted with 0–3 $R^{84}$; provided that when one of $R^{80}$ and $R^{81}$ is H or alkyl, then the other is not H or alkyl;

or, alternatively, $R^{80}$ and $R^{81}$, may be taken together with the shown divalent carbon radical to form:

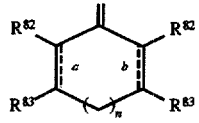

wherein:

$R^{82}$ and $R^{83}$ may be independently selected from the group: H; $R^{84}$; $C_1-C_{10}$ alkyl substituted with 0–3 $R^{84}$; $C_2-C_{10}$ alkenyl substituted with 0–3 $R^{84}$; $C_2-C_{10}$ alkynyl substituted with 0–3 $R^{84}$; aryl substituted with 0–3 $R^{84}$; heterocycle substituted with 0–3 $R^{84}$; and carbocycle substituted with 0–3 $R^{84}$;

or, alternatively, $R^{82}$, $R^{83}$ may be taken together to form a fused aromatic or heterocyclic ring;

a and b indicate the positions of optional double bonds and n is 0 or 1.

$R^{84}$ is independently selected at each occurrence from the group: =O, F, Cl, Br, I, —CF$_3$, —CN, —CO$_2$R$^{85}$, —C(=O)R$^{85}$, —C(=O)N(R$^{85}$)$_2$, —N(R$^{85}$)$_3^+$, —CH$_2$OR$^{85}$, —OC(=O)R$^{85}$, —OC(=O)OR$^{85a}$, —OR$^{85}$, —OC(=O)N(R$^{85}$)$_2$, —NR$^{85}$C(=O)R$^{85}$, —NR$^{86}$C(=O)OR$^{85a}$, —NR$^{85}$C(=O)N(R$^{85}$)$_2$, —NR$^{86}$SO$_2$N(R$^{85}$)$_2$, —NR$^{86}$SO$_2$R$^{85a}$, —SO$_3$H, SO$_3$Na, —SO$_2$R$^{85a}$, —SR$^{85}$, —S(=O)R$^{85a}$, —SO$_2$N(R$^{85}$)$_2$, —N(R$^{85}$)$_2$, —NHC(=NH)NHR$^{85}$, —C(=NH)NHR$^{85}$, =NOR$^{85}$, —C(=O)NHOR$^{85}$, —OCH$_2$CO$_2$H, 2-(1-morpholino)ethoxy; and $R^{85}$, $R^{85a}$, and $R^{86}$ are each independently selected at each occurrence from the group: hydrogen, C$_1$–C$_6$ alkyl.

2. The reagent of claim 1 wherein:

Q is a biologically active molecule selected from the group: IIb/IIIa receptor antagonists, IIb/IIIa receptor ligands, fibrin binding peptides, leukocyte binding peptides, chemotactic peptides, somatostatin analogs, and selectin binding peptides;

d' is 1 to 3;

L$_n$ is:
—(CR$^{55}$R$^{56}$)$_{g''}$—|Y$^1$(CR$^{55}$R$^{56}$)$_f$Y$^2$|$_f$—(CR$^{55}$R$^{56}$)$_{g''}$—, wherein:

g" is 0–5;

f is 0–5;

f' is 1–5;

Y$^1$ and Y$^2$, are independently selected at each occurrence from: O, NR$^{56}$, C=O, C(=O)O, OC(=O)O, C(=O)NH—, C=NR$^{56}$, S, SO, SO$_2$, SO$_3$, NHC(=O), (NH)$_2$C(=O), (NH)$_2$C=S;

R$^{55}$ and R$^{56}$ are independently selected at each occurrence from: hydrogen, C$_1$–C$_{10}$ alkyl, and alkaryl;

H$_z$ is a stable hydrazone of formula:

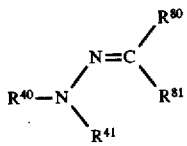

wherein,

R$^{40}$ is independently selected at each occurrence from the group: aryl substituted with 0–3 R$^{52}$, and heterocycle substituted with 0–3 R$^{52}$;

R$^{41}$ is independently selected from the group: hydrogen, aryl substituted with 0–1 R$^{52}$, C$_1$–C$_3$ alkyl substituted with 0–1 R$^{52}$, and a heterocycle substituted with 0–1 R$^{52}$;

R$^{52}$ is independently selected at each occurrence from the group: a bond to L$_n$, —CO$_2$R$^{53}$, —CH$_2$OR$^{53}$, —SO$_3$H, —SO$_2$R$^{53a}$, —N(R$^{53}$)$_2$, —NHC(=NH)NHR$^{53}$, and —OCH$_2$CO$_2$H;

R$^{53}$, R$^{53a}$ are each independently selected at each occurrence from the group: hydrogen and C$_1$–C$_3$ alkyl;

R$^{80}$ is independently selected at each occurrence from the group: —CO$_2$R$^{85}$; C$_2$–C$_5$ 1-alkene substituted with 0–3 R$^{84}$; C$_2$–C$_5$ 1-alkyne substituted with 0–3 R$^{84}$; aryl substituted with 0–3 R$^{84}$; unsaturated heterocycle substituted with 0–3 R$^{84}$;

R$^{81}$ is independently selected at each occurrence from the group: H and C$_1$–C$_5$ alkyl;

or, alternatively, R$^{80}$ and R$^{81}$, when taken together with the indicated divalent carbon radical form

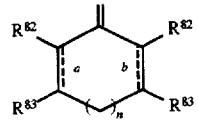

wherein R$^{82}$ and R$^{83}$ may be independently selected from the group: H and R$^{84}$;

or, alternatively, R$^{82}$, R$^{83}$ may be taken together to form a fused aromatic or heterocyclic ring;

a and b indicate the positions of optional double bonds and n is 0 or 1.

R$^{84}$ is independently selected at each occurrence from the group: —CO$_2$R$^{85}$, —C(=O)N(R$^{85}$)$_2$, —CH$_2$OR$^{85}$, —OC(=O)R$^{85}$ —OR$^{85}$, —SO$_3$H, —SO$_3$Na, —N(R$^{85}$)$_2$, —OCH$_2$CO$_2$H;

R$^{85}$ is independently selected at each occurrence from the group: hydrogen, C$_1$–C$_3$ alkyl.

3. The reagent of claim 2 wherein:

Q represents a biologically active molecule selected from the group: IIb/IIIa receptor antagonists and chemotactic peptides;

d' is 1;

L$_n$ is:
—(CR$^{55}$R$^{56}$)$_{g''}$—|Y$^1$(CR$^{55}$R$^{56}$)$_f$Y$^2$|$_f$—(CR$^{55}$R$^{56}$)$_{g''}$—, wherein:

g" is 0–5;

f is 0–5;

f' is 1–5;

Y$^1$ and Y$^2$, at each occurrence, are independently selected from: O, NR$^{56}$, C=O, C(=O)O, OC(=O)O, C(=O)NH—, C=NR$^{56}$, S, NHC(=O), (NH)$_2$C(=O), (NH)$_2$C=S;

R$^{55}$ and R$^{56}$ are hydrogen;

H$_z$ is a stable hydrazone of formula:

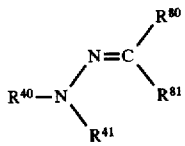

wherein,

R$^{40}$ is independently selected at each occurrence from the group: heterocycle substituted with R$^{52}$;

R$^{41}$ is hydrogen;

R$^{52}$ is a bond to L$_n$;

R$^{80}$ is independently selected from the group: —CO$_2$R$^{85}$; C$_2$–C$_3$ 1-alkene substituted with 0–1 R$^{84}$; aryl substituted with 0–1 R$^{84}$; unsaturated heterocycle substituted with 0–1 R$^{84}$;

R$^{81}$ is H;

R$^{84}$ is independently selected at each occurrence from the group: —CO$_2$R$^{85}$; —OR$^{85}$; —SO$_3$H; SO$_3$Na; —N(R$^{85}$)$_2$;

R$^{85}$ is independently selected at each occurrence from the group:

H and methyl.

4. A reagent according to claim 3, wherein Q is a cyclic IIb/IIIa receptor antagonist.

5. The reagents of claim 4 that are

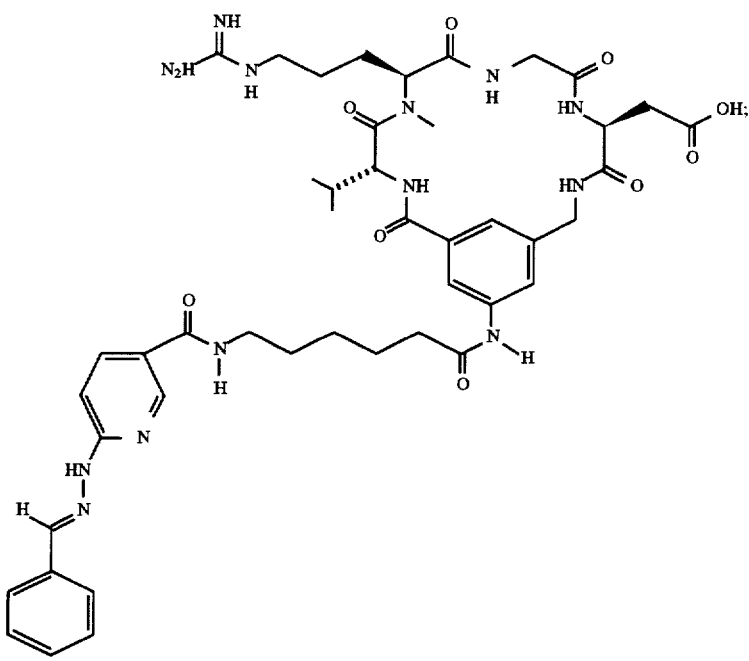
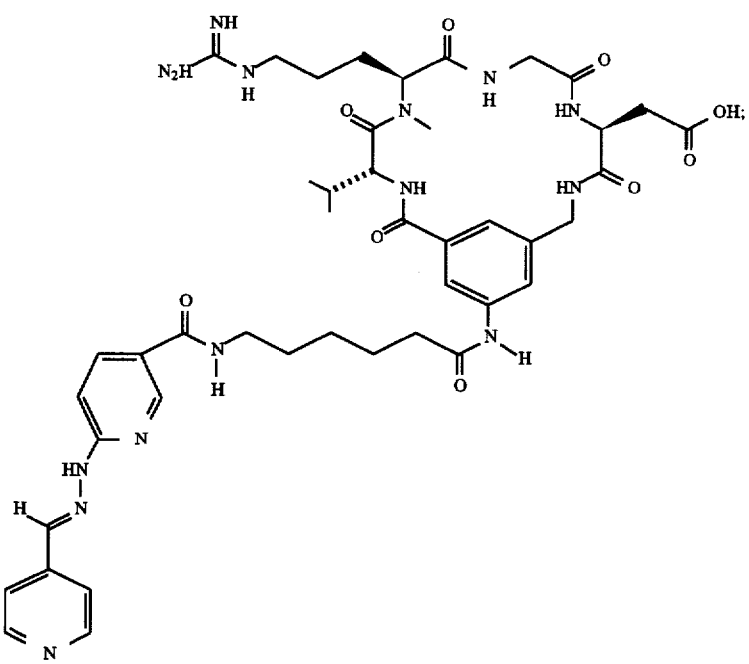

-continued
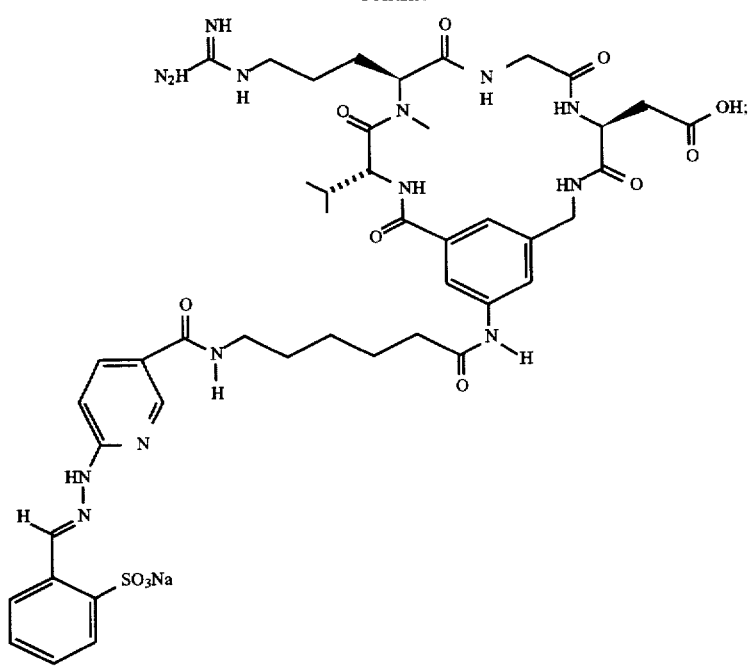
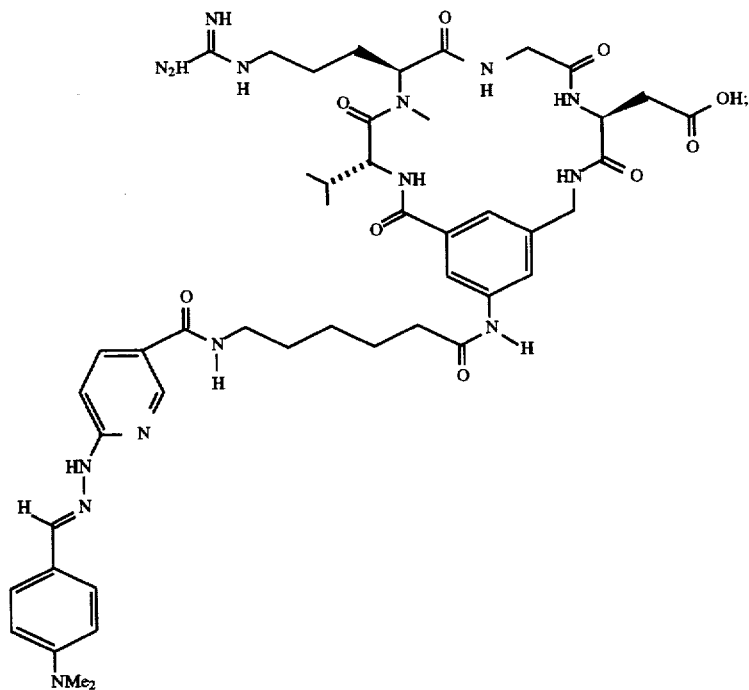

-continued
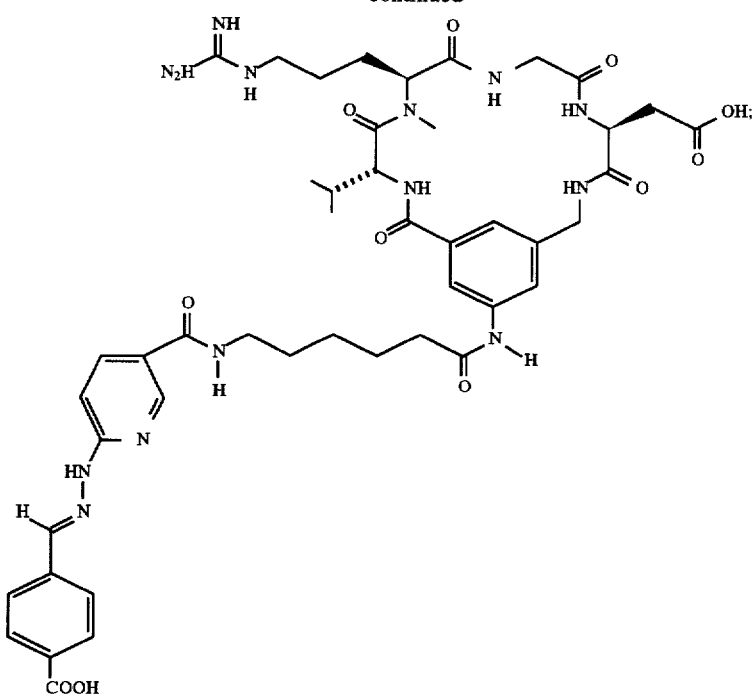
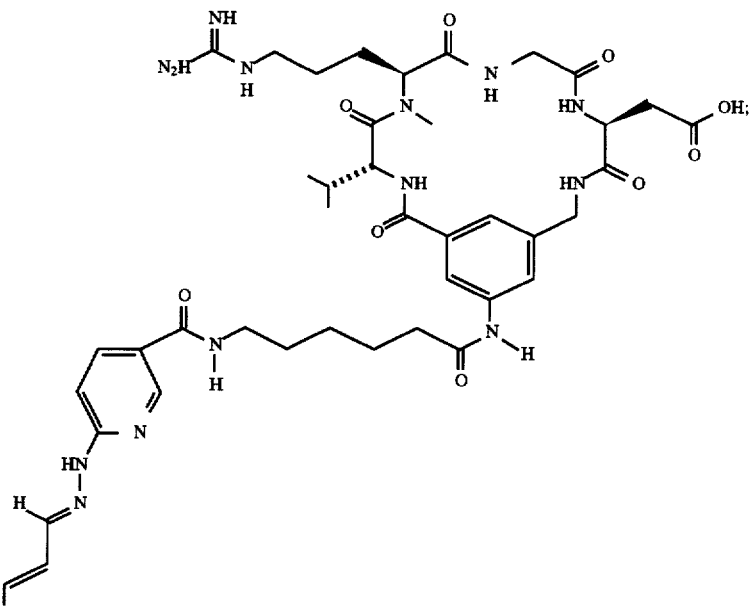

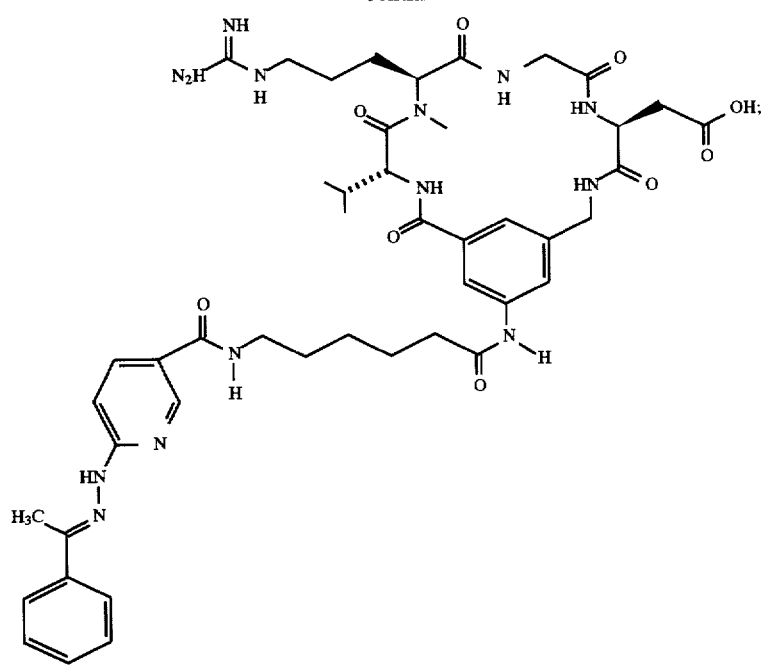
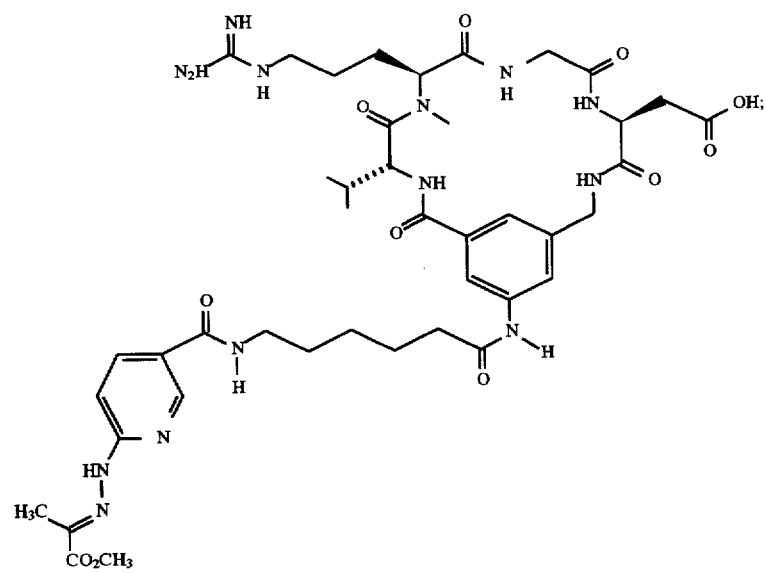

-continued
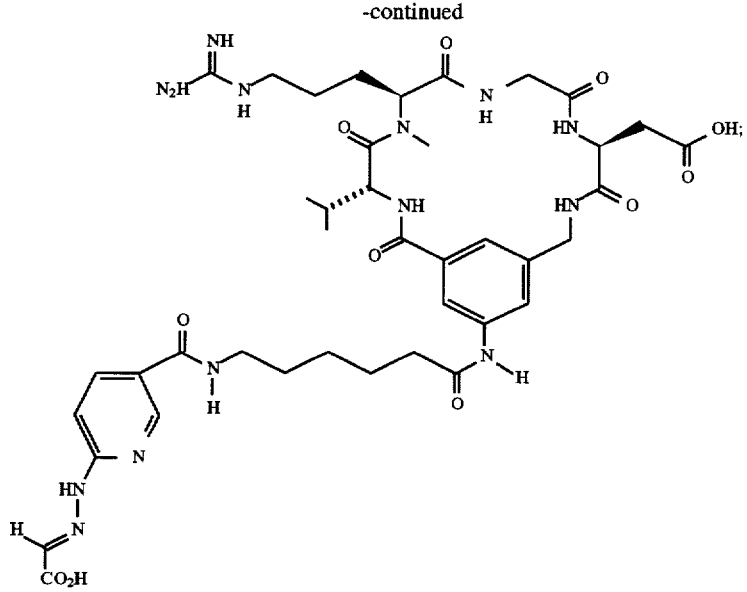
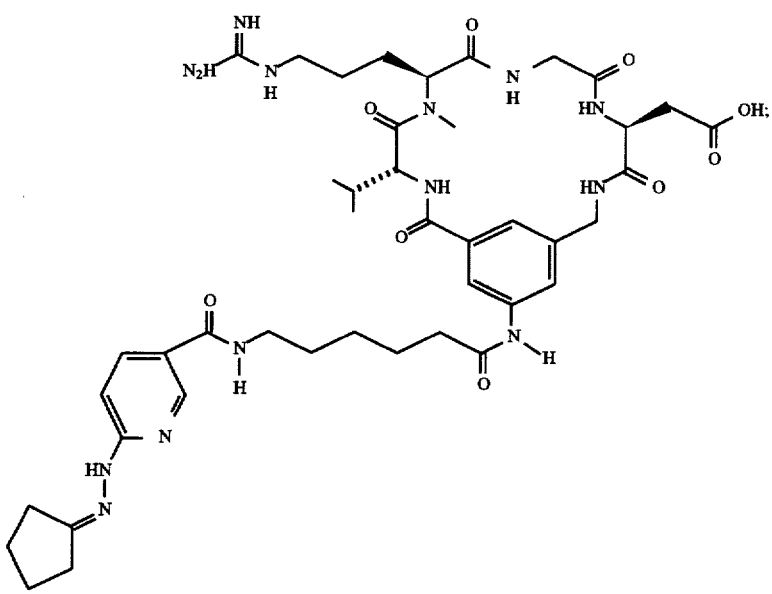

-continued

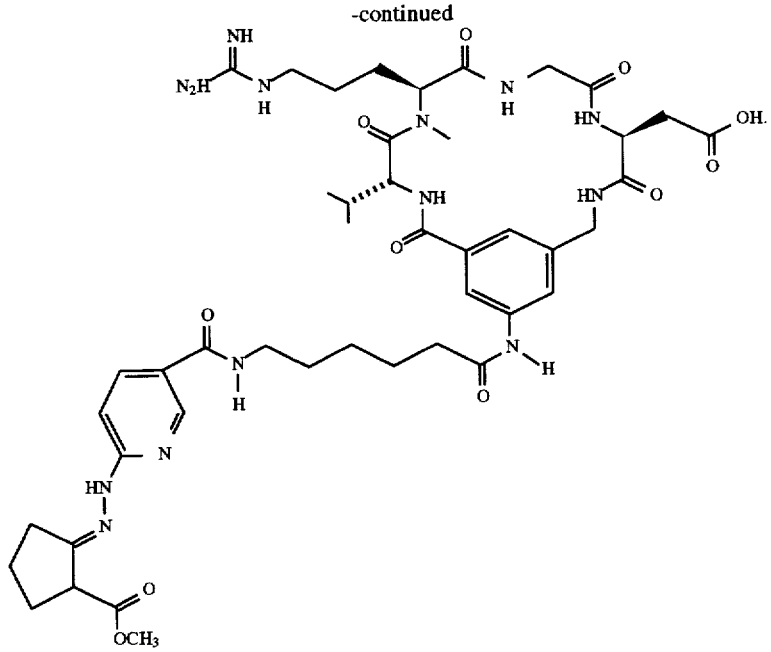

6. A kit for preparing a radiopharmaceutical comprising:
(a) a predetermined quantity of a sterile, pharmaceutically acceptable reagent of any of claims 1–3 and 4,
(b) a predetermined quantity of one or more sterile, pharmaceutically acceptable ancillary ligand(s);
(c) a predetermined quantity of a sterile, pharmaceutically acceptable reducing agent; and
(d) optionally, a predetermined quantity of a sterile, pharmaceutically acceptable component selected from the group:
transfer ligands, buffers, lyophilization aids, stabilization aids, solubilization aids and bacteriostats.

7. A kit for preparing a radiopharmaceutical comprising:
(a) a predetermined quantity of a sterile, pharmaceutically acceptable reagent of any of claims 1–3 and 4,
(b) a predetermined quantity of two sterile, pharmaceutically acceptable ancillary ligand(s);
(c) a predetermined quantity of a sterile, pharmaceutically acceptable reducing agent; and
(d) optionally, a predetermined quantity of a sterile, pharmaceutically acceptable component selected from the group: transfer ligands, buffers, lyophilization aids, stabilization aids, solubilization aids and bacteriostats.

* * * * *